United States Patent
Droste et al.

(10) Patent No.: US 9,501,616 B2
(45) Date of Patent: *Nov. 22, 2016

(54) PROCESSING OF DIGITAL DATA, IN PARTICULAR MEDICAL DATA BY A VIRTUAL MACHINE

(75) Inventors: Claudia Droste, Garching (DE); Klaus Breitschaft, Feldkirchen (DE);
(Continued)

(73) Assignee: Brainlab AG, Feldkirchen (DE)

( * ) Notice: Subject to any disclaimer, the term of this patent is extended or adjusted under 35 U.S.C. 154(b) by 357 days.

This patent is subject to a terminal disclaimer.

(21) Appl. No.: 14/001,289

(22) PCT Filed: Mar. 29, 2011

(86) PCT No.: PCT/EP2011/054839
§ 371 (c)(1),
(2), (4) Date: Aug. 23, 2013

(87) PCT Pub. No.: WO2012/130289
PCT Pub. Date: Oct. 4, 2012

(65) Prior Publication Data
US 2013/0339958 A1 Dec. 19, 2013

(51) Int. Cl.
*H04L 29/06* (2006.01)
*G06F 19/00* (2011.01)
(Continued)

(52) U.S. Cl.
CPC ............. *G06F 19/321* (2013.01); *G06F 21/41* (2013.01); *H04L 61/306* (2013.01)

(58) Field of Classification Search
CPC .................... G06F 19/321; G06F 21/41; H04L 61/306
(Continued)

(56) References Cited

U.S. PATENT DOCUMENTS 7,461,144 B1   12/2008   Beloussov et al.
7,484,245 B1 *  1/2009   Friedman ................ G06F 21/52
                                                        380/283
(Continued)

OTHER PUBLICATIONS

International Search Report for International Application No. PCT/EP2011/054839 dated May 9, 2012.

*Primary Examiner* — Michael S McNally
(74) *Attorney, Agent, or Firm* — Tucker Ellis LLP

(57) ABSTRACT

The present invention relates to a virtual machine (VM) for processing digital data (MD), in particular medical data by executing a digital data processing application program, in particular a medical data application program called MeDPAP, the virtual machine (VM) being a simulation of a computer, the virtual machine comprising at least the following components: • a MeDPAP controller (MC) which is constituted —so that it can be addressed by a Uniform Resource Identifier called VM-URI via a wide area network (WAN), —to support direct interoperable interaction with a client application (MCA) over the wide area network (WAN), —to assign a Uniform Resource Identifier called MeDPAP-URI to the MeDPAP, and —to send the assigned MeDPAP-URI to the client application via the wide area network (WAN); and • the MeDPAP which is constituted —to process the digital data (MD), —so that it can be addressed by the client application via the wide area network (WAN) by using the MeDPAP-URI, and —to support direct interaction with the client application over the wide area network for receiving instructions from the client application (MCA) to process the digital data.

15 Claims, 11 Drawing Sheets

Hardware and Software Structure of Medical Data Processing System (MEDProS)

(75) Inventors: Rainer Birkenbach, Erding (DE);
Michael Braun, Munich (DE); Klaus Neuner, Glonn (DE); Henrik Wist, Ottobrunn (DE)

(51) Int. Cl.
*G06F 21/41* (2013.01)
*H04L 29/12* (2006.01)

(58) Field of Classification Search
USPC .......................................................... 726/28
See application file for complete search history.

(56) References Cited

U.S. PATENT DOCUMENTS

| | | | |
|---|---|---|---|
| 7,577,722 B1 | 8/2009 | Khandekar et al. | |
| 7,591,006 B2* | 9/2009 | Werner | G06F 21/31 380/59 |
| 8,250,666 B2* | 8/2012 | Karabulut | G06F 21/52 717/120 |
| 8,695,102 B2* | 4/2014 | Bade | G06F 21/62 726/26 |
| 8,713,700 B2* | 4/2014 | Sobue | G06F 21/62 380/232 |
| 2003/0033367 A1 | 2/2003 | Itoh | |
| 2003/0182400 A1 | 9/2003 | Karagounis et al. | |
| 2006/0089967 A1 | 4/2006 | Gutmans et al. | |
| 2007/0043860 A1* | 2/2007 | Pabari | G06F 9/5072 709/224 |
| 2009/0288084 A1 | 11/2009 | Astete et al. | |

* cited by examiner

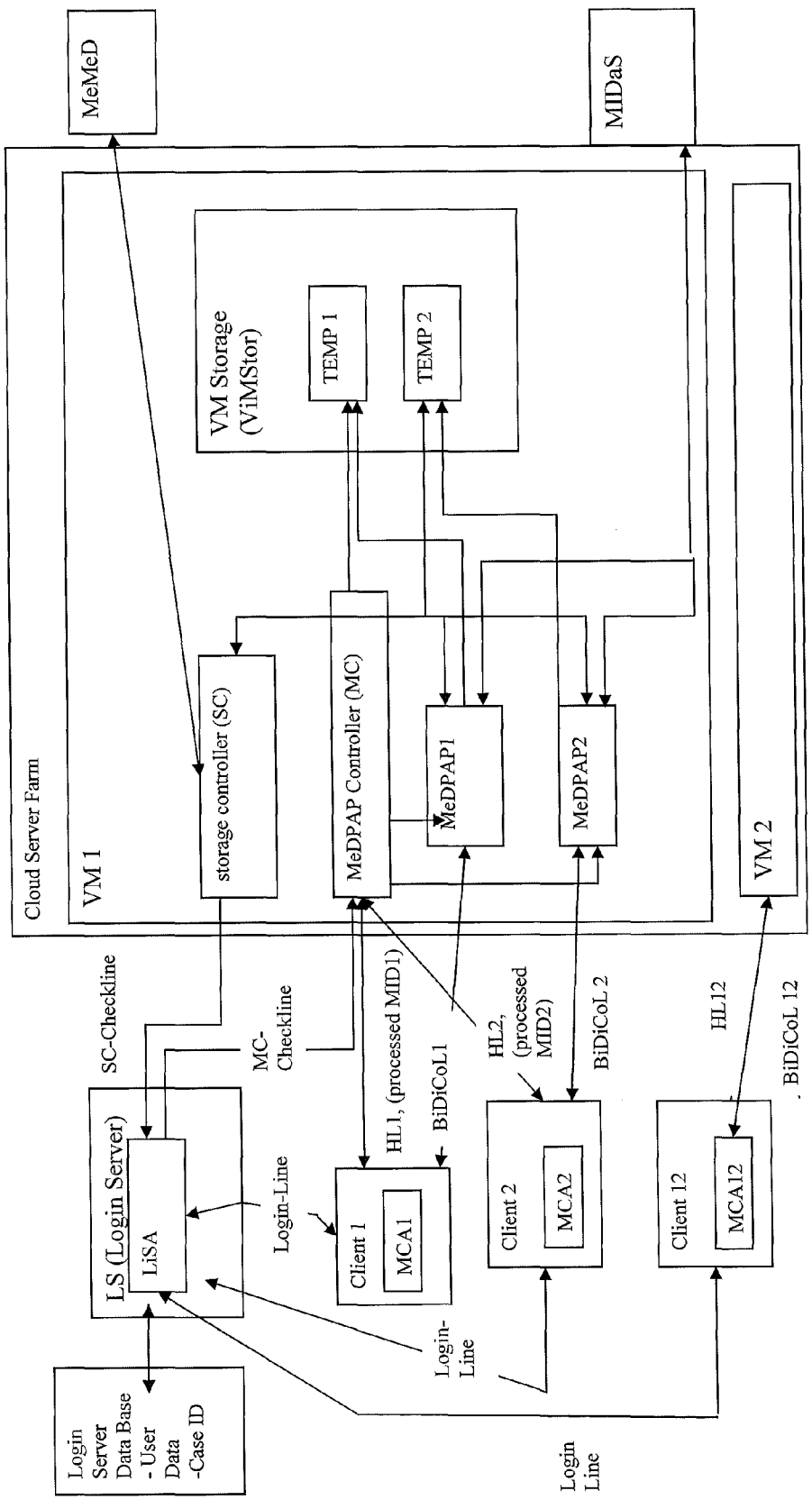
Fig. 1: Hardware and Software Structure of Medical Data Processing System (MEDProS)

Fig. 2: Login
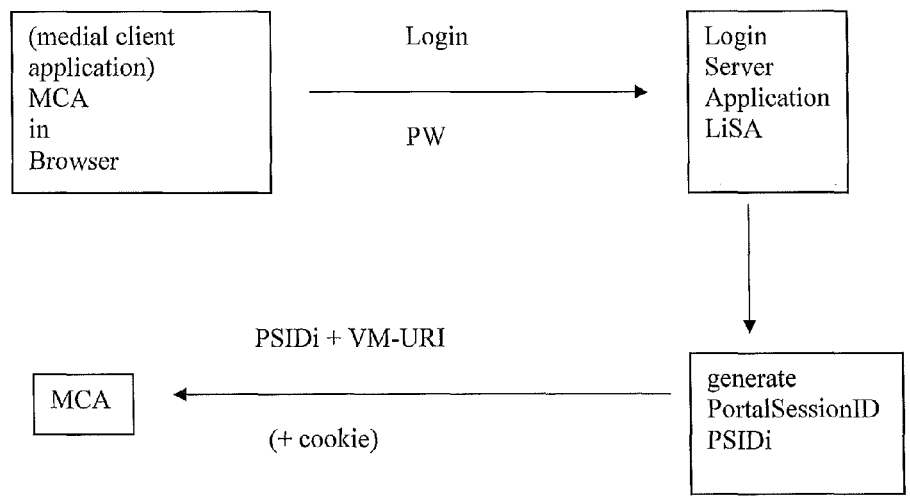
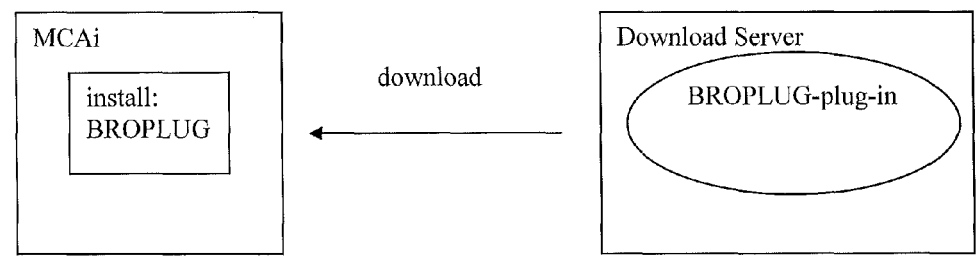
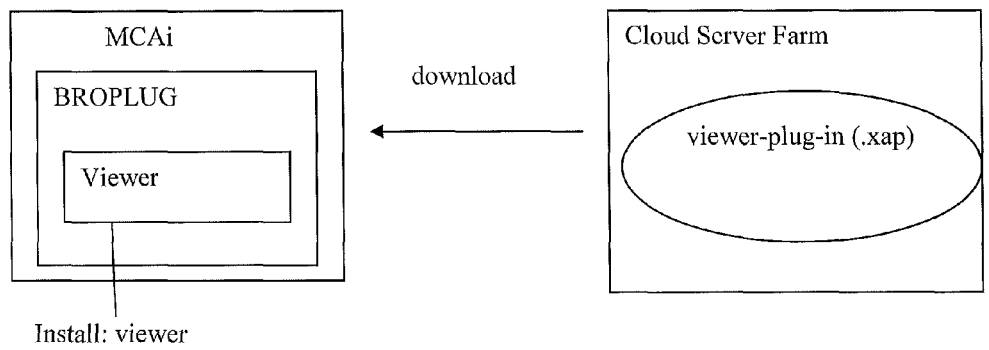

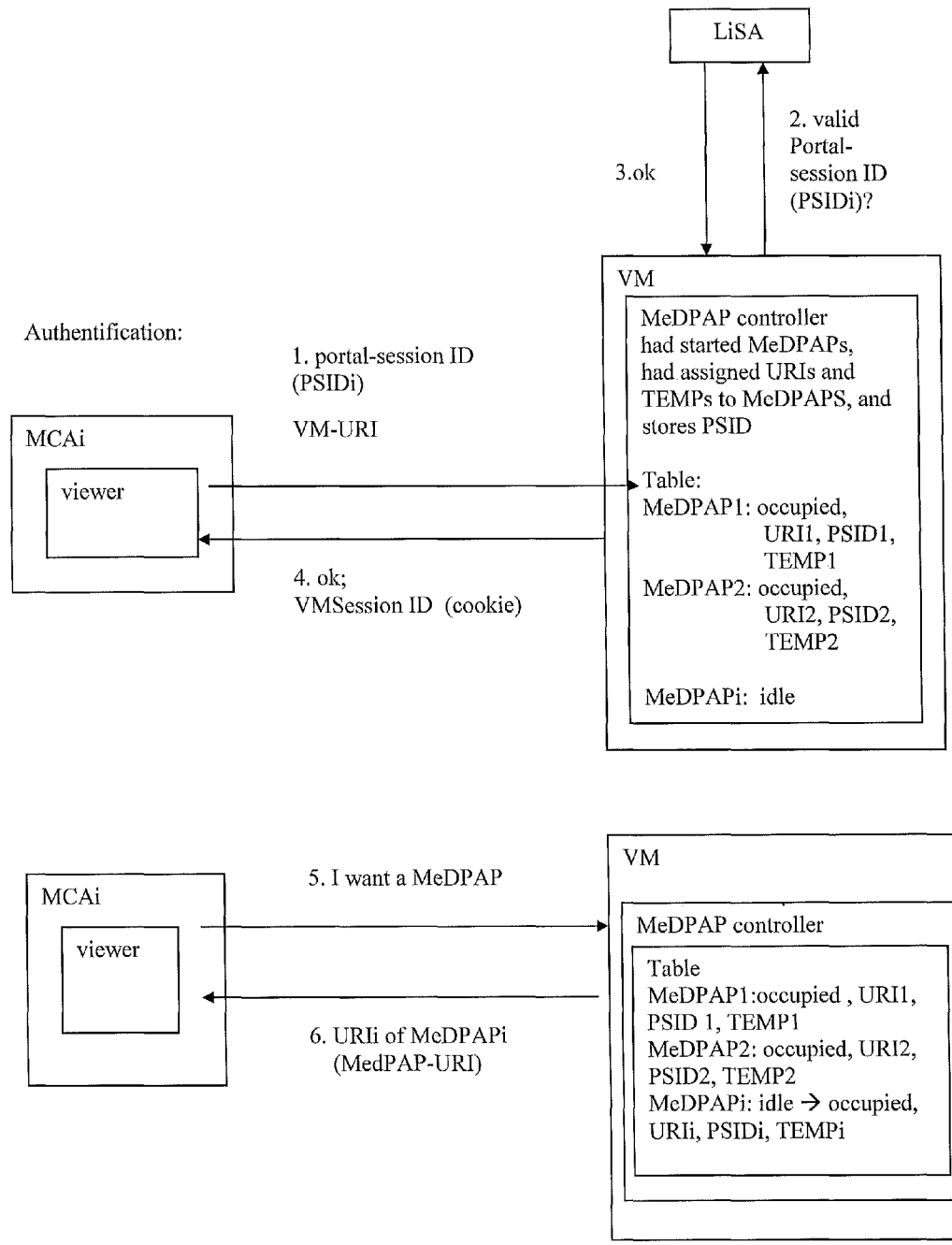
Fig. 3a: during start up of viewer

Fig. 3b:
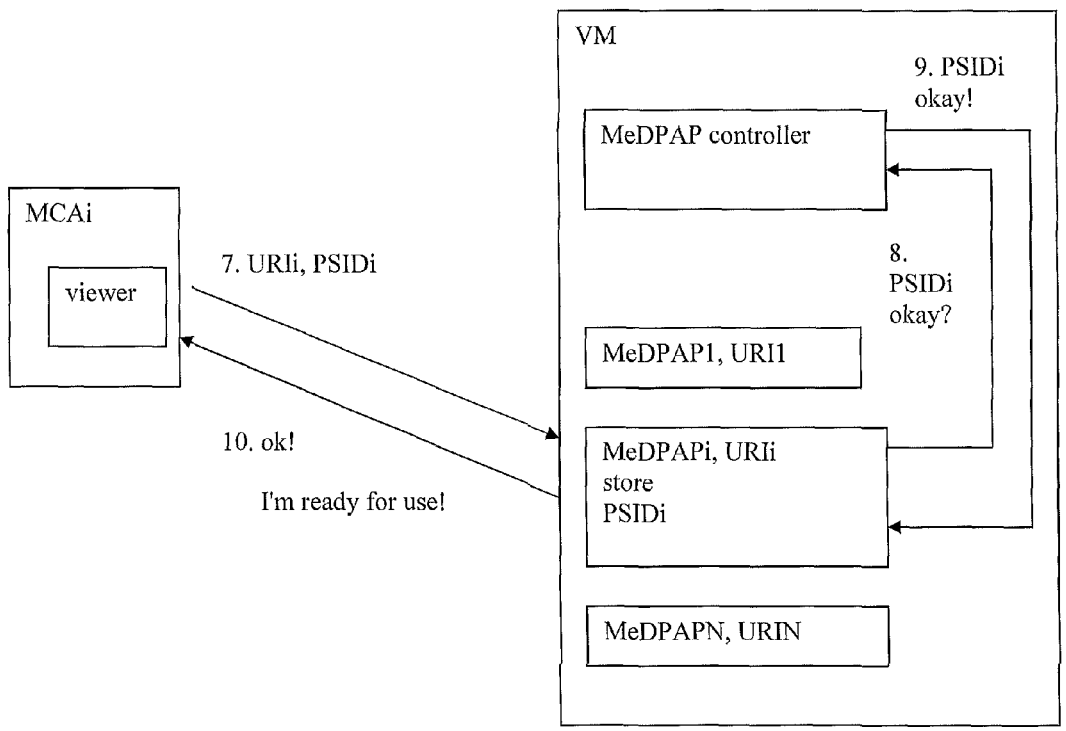
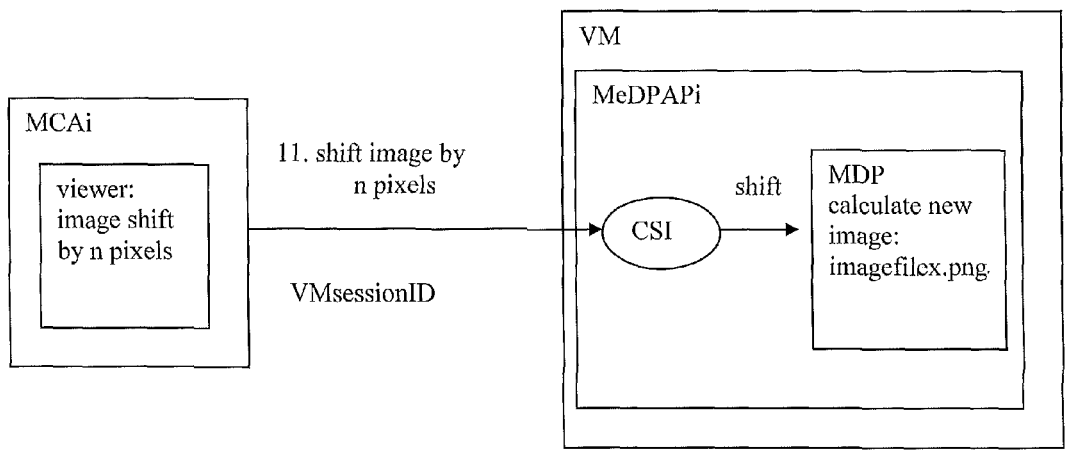

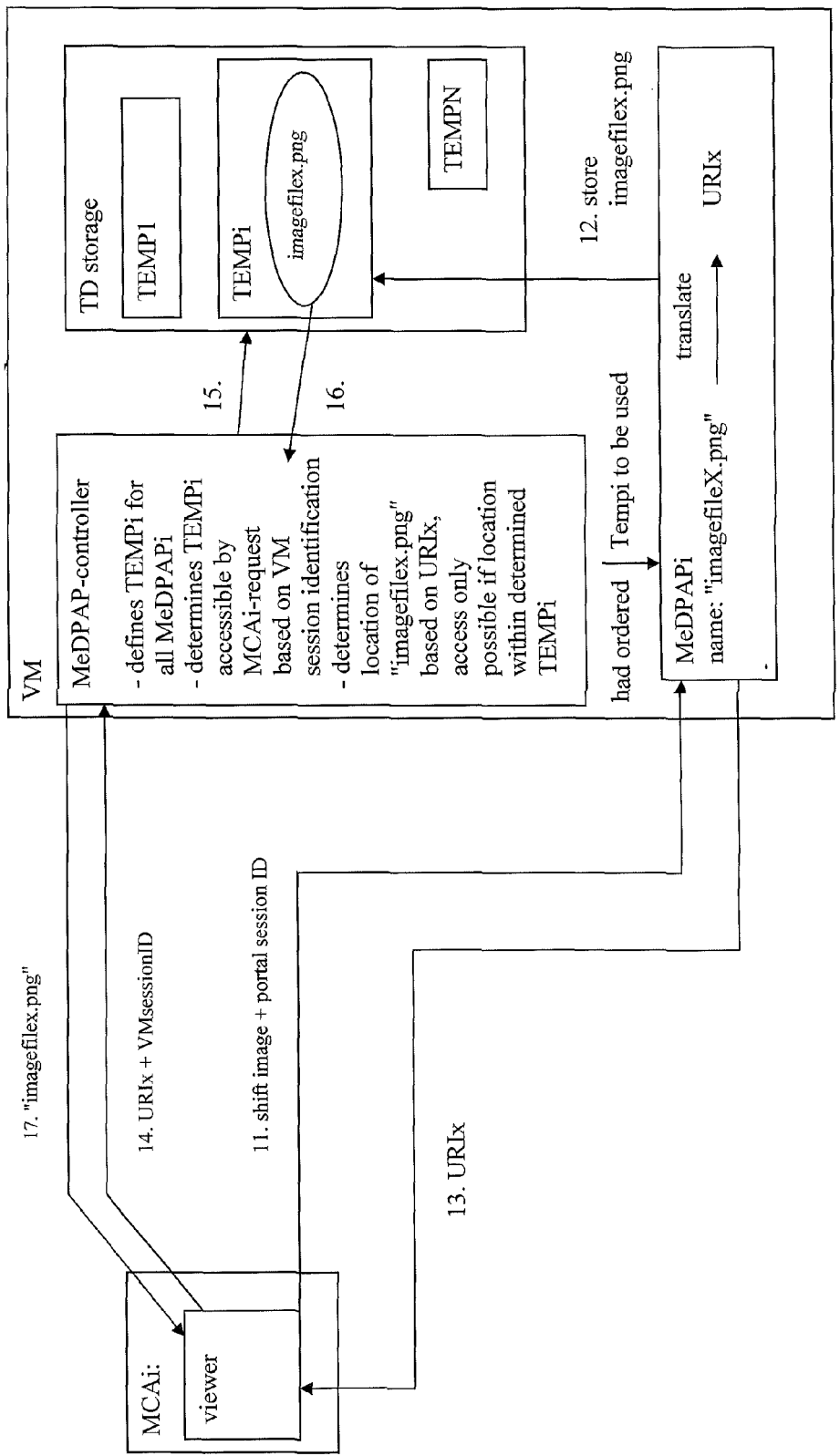
Fig. 4a: Image transfer MCAi ← VM

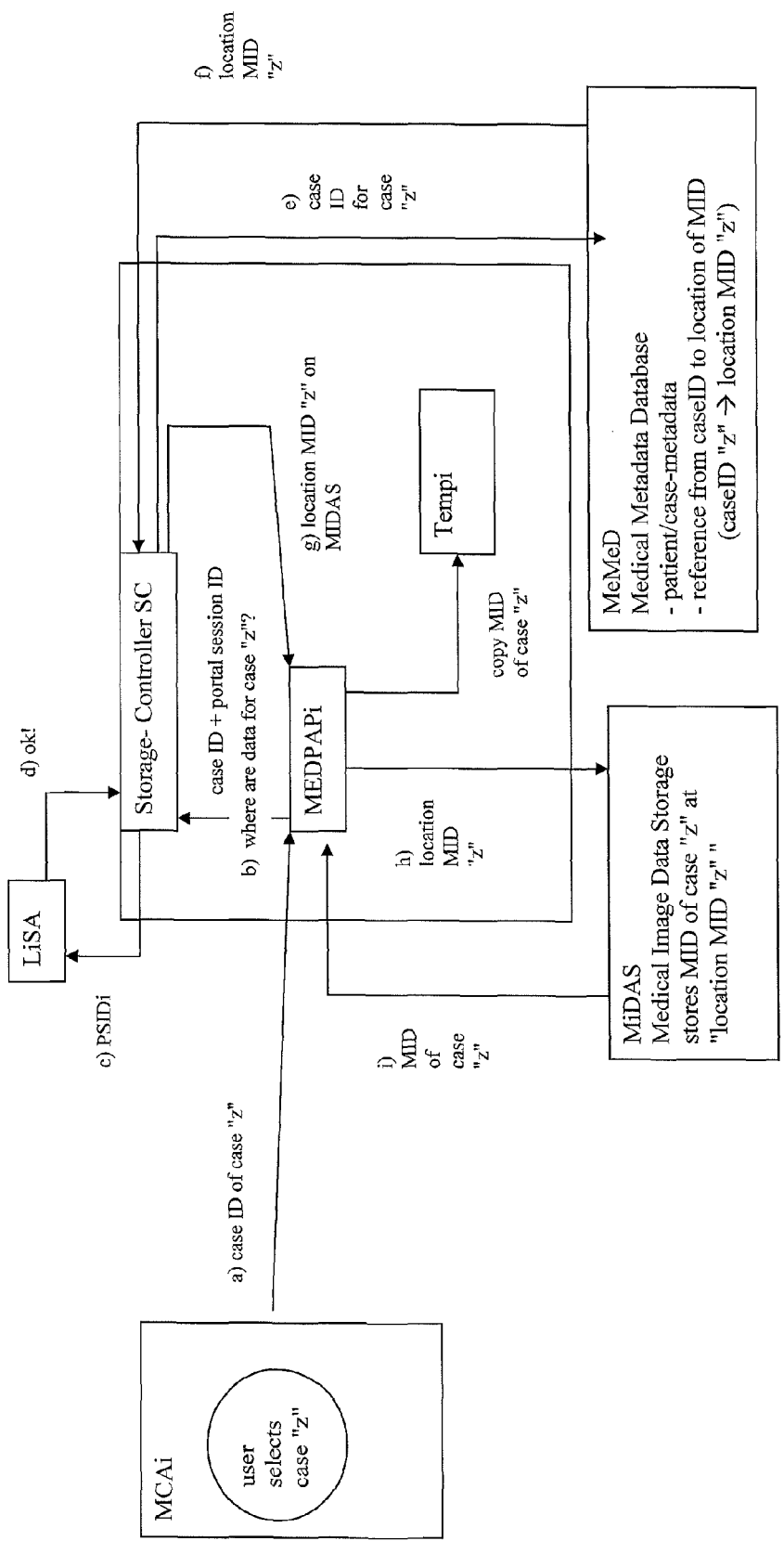
Fig. 5: Processing of Medical Data (MD) and in particular Medical Image Data (MID) (between step 10 and 11)

PROCESSING OF DIGITAL DATA, IN PARTICULAR MEDICAL DATA BY A VIRTUAL MACHINE

This application is a national phase of International Application No. PCT/EP2011/054839 filed Mar. 29, 2011 and published in the English language.

The present invention relates to the processing of digital data, in particular medical data by a virtual machine. The virtual machine is a simulation of a server. This simulation runs in particular on a computer system. The computer system comprises a number of computers (one, two or a plurality). Preferably, the processing capacity of the computer system is scalable. The computer system is in particular on a cloud computer system.

The present invention is in particular directed to the field of medical data. The medical data comprise in particular medical image data (like CT images or CBCT images or MRT images) which include a huge amount of data to be processed. In the following the term "medical data" is used instead of "digital data" although any other kind of digital data can be processed like image data or audio data in accordance with the present invention. The digital data are in particular data representing physical properties.

The object of the invention is to enable a fast processing of digital data by a virtual machine.

This problem is solved by the subject-matter of any appended independent claim. Advantages, advantageous features, advantageous embodiments and advantageous aspects of the present invention are disclosed in the following and contained in the subject-matter of the dependent claims. Different advantageous features can be combined in accordance with the invention as long as technically sensible and feasible. In particular, a feature of one embodiment which has the same or similar function of another feature of another embodiment can be exchanged. In particular, a feature of one embodiment which supplements a further function to another embodiment can be added to the other embodiment.

According to an embodiment a virtual machine for processing digital data, in particular medical data is provided. The processing of the digital data is performed by executing a digital data processing application program on the virtual machine. The digital data processing application program is in particular an executable program (having in particular the file extension ".exe"). The file of the digital data processing application program is in particular stored in the virtual machine. The digital data processing application program is in the following called "MeDPAP" and is in particular a medical data application program. As mentioned above, the virtual machine is in particular a simulation of a computer, in particular of a computer which works as a server and in particular which allows communication with another computer which works as a client. The virtual machine is in particular running on a cloud computer system, for instance on a server farm which provides services of cloud computing. The virtual machine is in particular a virtual computer, in particular a virtual server which is running on the cloud computer. Preferably at least one instance of a MeDPAP is running or ready to run on the virtual machine. As far as it is stated herein that the virtual machine "comprises" a (software) component (in particular a software component), e.g. an application and/or a program and/or a service, in particular the MeDPAP controller (see below) or a number of MeDPAPs, this means that the application (e.g. MeDPAP or MeDPAP controller) is running on the VM or is ready to run on the VM (in particular is loaded in the VM and ready to be started). As far as the term MeDPAP is used herein, it can be a MeDPAP which is ready to run or which is running. As far as the term MeDPAP controller is used it can be a MeDPAP controller which is ready to run or which is running. "Ready to run" means in particular that the MeDPAP controller can be started (e.g. via a call instruction) by the operating system of the VM.

The virtual machine which is abbreviated VM comprises in particular a VM data storage (which is abbreviated as ViMStor) for storing the digital data. As mentioned above, the digital data are in particular medical data. Therefore, the digital data are called MD. The ViMStor is preferably implemented as a part of a storage provided by a RAM-disc, alternatively or additionally it can be implemented on a hard disc.

The MeDPAP controller and the MeDPAP and optionally the ViMStor are examples for components of the virtual machine. There are in particular examples for components which have been loaded (in particular installed) into the virtual machine. For instance a RAM disk software has been installed.

The virtual machine further preferably comprises the MeDPAP controller as a running software component or as a software component which is ready to run. This software component is called MeDPAP controller and is abbreviated as MC. The MC is preferably stored on the VM. The MeDPAP controller is preferably an application program which has properties of a web service and is in particular implemented as a running web service. The MeDPAP controller has in particular at least one of the properties described in the following. The MeDPAP controller is running on the VM. The MeDPAP controller is constituted so that it can be addressed by a Uniform Resource Identifier. This Uniform Resource Identifier is called herein controller-URI (or also VM-URI). The MeDPAP controller is in particular an interface which allows communication of the virtual machine via a WAN (wide area network, e.g. internet) with a client application. To this end, the MeDPAP controller is preferably constituted to understand a language which allows communication between computer systems of the WAN independently of the platform and/or implementation used on the computer systems. In particular the MeDPAP controller is constituted to understand XML language. In particular the MeDPAP controller supports interoperable machine-to-machine interaction over the WAN (in particular the internet). In particular the MeDPAP controller supports interoperable interaction between a client application and the virtual machine over the WAN. Preferably, the MeDPAP controller has an interface which is described in a machine-processable format (in particular Web Services Description Language). In particular, the MeDPAP controller is constituted to interact with a client application using so called SOAP messages. The SOAP messages are preferably conveyed using HTTP with an XML serialisation in conjunction with other web-related standards. The so called SOAP is a protocol specification for exchanging structured information in the implementation of web services. Preferably, the message format is XML (Extensible Markup Language). In particular the protocol used by the MeDPAP controller (in particular the SOAP) relies on the XML and preferably on other application layer protocols, in particular Remote Procedure Call (RPC) and Hypertext Transfer Protocol (HTTP).

The WAN is not part of the VM (and in particular the MeDPAP controller) and the VM (and in particular the MeDPAP controller) is connected to or is constituted to be connected to the WAN.

Preferably, the MeDPAP controller is also constituted to start the execution of the digital data processing application program which is abbreviated as MeDPAP. To this end, preferably the MeDPAP is stored on the virtual machine. Preferably, the MeDPAP controller is constituted to start the MeDPAP a plurality of times so that a plurality of MeDPAPs (to be more clear a plurality of MeDPAP instances) are running simultaneously on the virtual machine. That is, the MeDPAP controller is preferably constituted to start execution of the MeDPAP a plurality of times. As a consequence, the plurality of MeDPAPs are running simultaneously on the virtual machine. The number of MeDPAP instances is preferably chosen in dependence on the processing power of the VM. Each of the plurality of MeDPAP instances is preferably controllable, in particular (identifiable and) independently addressable by the MeDPAP controller. To this end, the individual process IDs and/or process handles of the MeDPAP instances are preferably used by the MeDPAP controller. The MeDPAP controller is in particular the parent to which the child (i.e. the MeDPAP instance) in particular sends the process ID. As far as in the following it is mentioned that a MeDPAP is running, this means that a MeDPAP instance is running. Furthermore, MeDPAPi will be an example for a MeDPAP instance in the following. As far as the constitution and/or ability of a MeDPAP is described, this refers to the constitution and/or ability of the MeDPAP when it is running, i.e. when the MeDPAP is a MeDPAP instance. If the description refers to an action performed by a MeDPAP, this means that the action is performed by a running MeDPAP, i.e. a MeDPAP instance. Of course it is possible to generate a plurality of MeDPAPs (in particular MeDPAP instances) by either starting (calling) one and the same MeDPAP (MeDPAP.exe) a plurality of times or by starting a plurality of MeDPAPs (MeDPAP.exes). If it is described herein that MeDPAPs are constituted for something this means that the running MeDPAPs are constituted for this something if started a plurality of times or that the plurality of MeDPAP.exes (which are ready to run on the VM) are constituted for this something is started. "MeDPAP.exe" is an example for the program file MeDPAP, i.e. the MeDPAP file. The MeDPAP file is preferably a compiled program (however could also be implemented by using an interpreter).

The MeDPAP controller is in particular a software system designed to support the above-mentioned interoperable machine-to-machine interaction over a network. In particular the MeDPAP controller is a web service as defined by the World Wide Web Consortium (W3C).

The virtual machine is in particular defined by the operating system. In particular one virtual machine has one operating system, in particular a server operating system like Windows Server 2008, Windows Server 2003, Windows Server 2008R2, Linux, and Unix.

The MeDPAP controller is in particular constituted to send a Uniform Resource Identifier called MeDPAP-URI to the client application. Preferably, the MeDPAP controller assigns the MeDPAP-URI to the MeDPAP, for instance by storing a reference between the process handle and/or the process ID of the MeDPAPi and the MeDPAP-URI. Preferably, the assignment is stored. In particular the MeDPAP controller is constituted to select one of a plurality of available MeDPAP-URIs (which are in particular predefined) and to assign the selected MeDPAP-URI to the MeDPAPi. In particular in case there are plurality of MeDPAPs, the selected MedPAR-URI is assigned to one of the plurality of MeDPAP instances so that different MeDPAP-URIs are assigned to the MeDPAP instances. In other words, each MeDPAP-URI is exclusive for one of the MeDPAP instances. In particular the assignment between the MeDPAP instances and the MeDPAP-URIs can be stored in a table. Preferably the MeDPAP controller also stores an assignment between client applications and MeDPAP instances. That is, preferably each client application is exclusively assigned one MeDPAP-URI and one MeDPAP instance by the MeDPAP controller. The MeDPAP controller preferably stores this assignment, for instance in a table.

The MeDPAP controller is preferably an application which runs on a web server. As far as it is mentioned herein that the MeDPAP controller is constituted for something, this means that the running MeDPAP controller is constituted for this something. The web server can be for instance a IIS web server (Internet Information Services from Microsoft) or an APACHE web server. The web server is in particular a software component of the server operating system. Access to the virtual machine (where the web server is running) by a user can be performed for instance via a protocol (e.g. remote desktop protocol which provides a user with a graphical interface to another computer). The web server preferably provides static and dynamic content. As mentioned above, the MeDPAP controller (and preferably also the later mentioned storage service) is an application which runs on the web server (for instance IIS). The application has preferably a web service part (having for instance an extension ".asmx") and comprises preferably also assemblies (having for instance extension ".dll"). Preferably, the application (for instance MeDPAP controller and/or storage service) also has a handler for handling the URI, in particular a HTTP-handler. The URI-handler determines the location of a file in the ViMStor (reads files out of the ViMStor and preferably also checks a VM session ID as will be described later).

The MeDPAP is preferably an executable application program (in particular the file of which having the ending ".exe"). The MeDPAP (i.e. the MeDPAP instance) is preferably running on the server operating system. Preferably, the executable file representing the MeDPAP is stored in a storage of the virtual machine, in particular in a hard disc. The MeDPAP can for instance be programmed in C++ language in particular by using a so called .net-framework (of Microsoft®) and preferably also comprises a web service interface. The web service included in the MeDPAP is in particular a so called WCF (Windows Communication Foundation) web service. As mentioned above, the MeDPAP is preferably constituted so it can be started by the MeDPAP controller. The features of the MeDPAP described herein in particular relate to a MeDPAP (i.e. a MeDPAP instance) which is running on the virtual machine. In particular as far as stated that the MeDPAP is constituted for something, this means that the MeDPAP is constituted for (is able to do) this something in case the MeDPAP is running on the virtual machine. That is, the MeDPAP instance is able to do this something. As far as it is not explicitly mentioned otherwise herein, the term "MeDPAP" refers to the program which is running on the virtual machine (i.e. to the MeDPAP instance) and not to the file (for instance MeDPAP.exe) which represents the MeDPAP and which can be started by the MeDPAP controller to generate a (running) MeDPAP (i.e. a MeDPAP instance). A MeDPAP instance is in particular no longer existent after it had been stopped.

The MeDPAP is preferably constituted to process the digital data, in particular the medical data. In particular the MeDPAP is constituted to perform image processing by processing image data. In particular, the MeDPAP is constituted to generate image files which represent processed image data. For instance the image file represents a defined part of an image or a defined sub image or a processed image, in particular a sequence of processed images (e.g. an image of which the contrast is enhanced or which has been zoomed) or a reconstructed image like a DRR (digitally reconstructed radiograph), or fusioned or morphed images, streamed content like video stream or streamed images, 3D video streams, animated images etc.).

Preferably, the MeDPAP is constituted so that the MeDPAP can be addressed by the client application by using the MeDPAP-URI. That is, the client application (called MCA) can directly address the MeDPAP which is running within the virtual machine without needing the MeDPAP controller or any kind of web service as an interface. This allows to speed up the response time of the virtual machine in case the client application instructs the virtual machine (to be more specific the assigned MeDPAP instance) to process the digital data. To this end, the executable MeDPAP file preferably includes a part which operates as a web service when the MeDPAP is running. In particular since the web service is part of a single (compiled) program (the MeDPAP), the instructions received directly from the client application can initiate the processing of the digital data more quickly. Moreover, since each MeDPAP instance has its own unique MeDPAP-URI and since this MeDPAP-URI is given only to one client application, the MeDPAP instance can only receive instructions to process, digital data by one client application. In this way, data cross talk (i.e. unauthorized and/or inadvertent access to data assigned to another client application) is avoided compared to the case that several client applications instruct the same MeDPAP instance. This is in particular of importance in the medical field where a reliable result of data processing (in particular processing of medical image data) is of advantage as noted by the inventors.

A MeDPAP-URI can be constructed as follows: https://VMi-URI/MEDPAPi. VMi is the i-th virtual machine. That is, the present invention is also directed to a set of the virtual machines (VMi, i=1 . . . M) which set comprises in particular a plurality of the VMs.

Preferably, the MeDPAP supports direct interoperable interaction with the client application over the network (e.g. internet). To this end, the MeDPAP preferably comprises a WAN interface, in particular an HTML interface. In this way, the MeDPAP can receive instructions from the client application which client application is called "MCA" (for medical client application) in order to process the digital data (MD) which are in particular stored in the VM data storage (which is part of the virtual machine).

It is also possible that the digital data are stored outside the virtual machine. However, according to a preferred embodiment, the digital data are stored inside the virtual machine and in particular a temporary storage (like a RAM disk) in order to increase processing speed and in particular reduce the risk of data leakage and data cross talk.

In order to promote the processing speed and in order to reduce the risk of data cross talk, preferably an exclusive storage space is assigned to each of the MeDPAP instances. The storage space is located in particular within the VM data storage and in particular within a RAM disk. The processed digital data are preferably placed within a file called Prodaf ("processed data file") by the MeDPAPi. Preferably the file is stored in the aforementioned storage space assigned to the MeDPAPi. The location of the Prodaf is preferably translated into a Prodaf-URI. Assume that an individual Prodaf has the name "Prodafx" then the Prodaf-URI assigned to Prodafx is called herein Prodaf-URIx. The location of the Prodaf is preferably within the aforementioned storage space. According to a less preferred embodiment, the location is somewhere else, for instance in a separate remote server farm providing hard disk space. Preferably the MeDPAP is constituted to send the Prodaf-URI (which represents the location of the Prodaf) to the client application (i.e. that client application which is assigned to the MeDPAP which determined the Prodaf-URI). In the following, the storage space is called TEMPi and is assigned to a particular one (called MeDPAPi) of the MeDPAPs.

The MeDPAP controller is preferably constituted to receive the Prodaf-URI (called Prodaf-URIx) from the client application. In other words, the client application (in particular caches and) sends the Prodaf-URI which it had received from the MeDPAP to the MeDPAP controller. The MeDPAP controller re-translates the received Prodaf-URI (Prodaf-URIx) into the location of the Prodaf. Then the MeDPAP controller can read the Prodaf based on the determined location of the Prodaf. In particular, in case of a fixedly assigned (and in particular exclusively assigned) storage space for the MeDPAP (which has generated the Prodaf-URI and the Prodaf), the MeDPAP controller is constituted to look for the Prodaf only within the assigned storage space (TEMPi). In this way, it is assured that the MeDPAP controller does not access a file of one of the other MeDPAPs and does not send such a file to the client application. Again this reduces the risk of data cross talk. Furthermore, using a Prodaf-URI allows the client application to cache the image by just caching the Prodaf-URI. In particular the browser plugin takes advantages of the browser caching functionality. The browser plug-in in the client application is called BROPLUG. In particular there is a bijective relationship between the individual client applications having a communication session with the virtual machine and the individual storage spaces (TEMPS) so that one of the client applications (e.g. MCAi) can only receive digital data (Prodafs) from one of the storage spaces (e.g. TEMPi).

Furthermore, there is a bijective direct communication between the individual client applications and the individual MeDPAPs (i.e. MeDPAP instances) so that one MeDPAP (i.e. one MeDPAP instance) is processing the digital data only for one client application. Preferably, if the communication session of a client application ends, then the exclusively assigned MeDPAP (i.e. MeDPAP instance) is stopped by the MeDPAP controller. Preferably, the MeDPAP controller is constituted to start a MeDPAP on the virtual machine. The MeDPAPs can be on reserve, that is the MeDPAP is running but idle, i.e. there is no communication established between the idle MeDPAP (i.e. idle MeDPAP instance) and a client application. On the other hand, if a client application starts communication with a virtual machine, it is not necessary to start the MeDPAP (i.e. MeDPAP instance) but there is already available an idle MeDPAP. The status of the MeDPAP (i.e. MeDPAP instance) changes from idle to occupied if the MeDPAP (i.e. MeDPAP instance) is assigned to a client application by the MeDPAP controller. This is in particular done by assigning the MeDPAP-URI to the MeDPAP (i.e. MeDPAP instance) when sending the MeDPAP-URI to the client application. The MeDPAP-URI can be assigned by sending a string representing the MeDPAP-URI. The sending can be within the virtual machine from the MeDPAP controller to the MeDPAP (i.e. MeDPAP instance), in particular to that part (CSI) of the MeDPAP (i.e. MeDPAP instance) which serves as a network interface (in particular a web service).

According to the above described embodiment, the MeDPAP controller sends the Prodaf to the client application. According to another embodiment, the MeDPAP sends the Prodaf directly to the client application. The above described embodiment is preferred since this reduces the workload of the MeDPAP and increases the processing speed of the MeDPAP.

In order to identify the client applications which are contacting the MeDPAP controller, the MeDPAP controller preferably generates an individual identifier called VM session ID for each communication session with one of the client applications. That is one VM session ID is exclusively assigned to each of the client applications. The VM session ID is valid as long as the communication session is active. Preferably, the MeDPAP controller stores an assignment between at least two (and preferably all) of the following: VM session ID, MeDPAP, MeDPAP-URI, storage space (TEMPi) and portal session ID (an individual session ID given to the client application by a login server application called LiSA which will be explained later and which is also individual for the client application). Thus, there are preferably a plurality of assignments (links) in order to assure that there is no data cross talk between different MeDPAP instances while assuring fast data processing due to the bijective direct communication link between the client applications and the MeDPAPs. That is for a client application MCAi one MeDPAPi instance (which is a started MeDPAP.exe) is working. A "MeDPAPi instance" is called in the following just "MeDPAPi".

Preferably, the MeDPAP controller holds an assignment (for instance a table) where a process ID of a MeDPAP is mapped to the process handle. Preferably, the process handle is also mapped to the assigned TEMPi. Preferably, the MeDPAP controller holds such an assignment (in particular a table) for a plurality of MeDPAP instances. In particular, the MeDPAPi is a child process to the MeDPAP controller (which is a parent). In particular, the process handle (mapped to the MeDPAPi) is used to stop the MeDPAPi and/or to monitor if the MeDPAPi is stopped (for instance intentionally or by a crash). In particular, the process handle is used to restart the MeDPAPi for instance if it has been detected (by the monitoring) that the MeDPAPi has stopped. This allows in particular for an automatic restart of a MeDPAPi if there was a crash.

Preferably, the MeDPAP instances (which have been started by the MeDPAP controller) run in the same user context as the MeDPAP controller. In particular the MeDPAP controller inherits the user context to the MeDPAP instances which have been started by the MeDPAP controller.

As mentioned above, preferably each communication session between a client application and the virtual machine that is a communication between the client application and the MeDPAP controller has its own VM session ID. The VM session ID is in particular checked by the MeDPAP controller when it is received. Only if the checking result is positive, that is if the received VM session ID corresponds to the VM session ID stored by the MeDPAP controller, then the request of the client is processed.

In particular, the client application is in the possession of a session ID which is preferably the above-mentioned portal session ID. This portal session ID is preferably given to the client application by the LiSA. The portal session ID is in particular individual and exclusive for the client application. That is each client application (MCAi) has an exclusive portal session ID.

The portal session ID is preferably sent from the client application to the MeDPAP controller. Preferably, the MeDPAP controller checks the validity of the portal session ID by contacting the LiSA. The MeDPAP controller preferably assigns (maps) the portal session ID to the client application MCAi (for instance by storing an assignment between the portal session ID and an identifier for MCAi in a table). Preferably, the client application (MCAi) sends the portal session ID to the assigned MeDPAP instance (MeDPAPi). The MeDPAPi preferably stores the received portal session ID. This allows for instance the MeDPAPi to check whether later requests of the MCAi are valid. Preferably, the MCAi always sends the portal session ID to the MeDPAPi together with a request.

The MeDPAPi is in particular configured to store the portal session ID at the beginning of the communication session with the client application.

Once the MeDPAPi has stored the portal session ID, preferably the MeDPAP does not accept any other requests which do not include the portal session ID from the client. Thus the MeDPAPi is exclusively occupied by the client application which is in the possession of the portal session ID and blocks any other attempts from other client applications to request processing.

As mentioned before, preferably there is an assignment (link) between the portal session ID and an individual MeDPAP and this assignment is stored preferably by the MeDPAP controller. In case a communication session between the virtual machine and a client application ends (for instance due to timeout or if the client application performs a logoff procedure), then the MeDPAP controller stops preferably the MeDPAP which had processed the medical data for the client application MCAi (for which the communication session has ended). Preferably, the MeDPAP controller additionally erases any data stored in the storage space (TEMPi) assigned to the MeDPAP which has been stopped. The term "erase" means herein to encompass any types of detecting or erasing. The same applies for the term "delete".

As mentioned above, the MeDPAP controller is in particular constituted to start a new MeDPAP. Preferably, the MeDPAP controller checks whether the storage space assigned to the new MeDPAP is free, i.e. the MeDPAP controller checks whether all previous data have been erased in the storage space. Also this reduces the risk of data cross talk and data leakage. Preferably, the MeDPAP controller assigns the free storage space to the MeDPAP after the checking result is positive (i.e. the storage space is confirmed to be empty). Alternatively or additionally the MeDPAP erases the storage space or checks its erased status, before the MeDPAP is assigned to a client application (in particular when the MeDPAP is started).

Preferably, the MeDPAP controller monitors the number of MeDPAPs in the virtual machine, i.e. the number of running MeDPAPs (for instance by using process ID and/or process handle). As mentioned above, a MeDPAP controller can in particular start and stop a MeDPAP. In order to maintain the number of MeDPAPs (running on the VM) constant, the MeDPAP controller preferably starts a new MeDPAP in case the number of MeDPAPs is below a predetermined threshold. In this way, it is enabled that idle MeDPAP instances are ready to be used by new client applications.

As mentioned above, there is preferably a bijective relationship between the MeDPAP instances and the client applications and thus between active communication sessions and the MeDPAP instances. The communication sessions can be identified by the portal session ID. Preferably, the MeDPAP controller monitors the number of MeDPAPs assigned to a communication session. Generally, there is an upper limit of MeDPAPs which are running on one of the virtual machines. In case the number of occupied MeDPAPs increases, in particular increases above a predefined threshold value, then the MeDPAP controller reports the number of occupied MeDPAPs to a server application which is in particular the above mentioned login server application (abbreviated as LiSA). The task of the LiSA is to allow a client application to login into the LiSA which in particular checks username and password of the client application and assigns a session identifier which is preferably the above-mentioned portal session ID to the client application and preferably also informs the client application about the URI of the VM assigned to the client application by the LiSA. This URI is in particular the above-mentioned VM-URI (or controller URI). Preferably, the MeDPAP controller receives the portal session ID from the client application (which addresses the VM-URI) and checks its validity by contacting the LiSA. Thus the MeDPAP controller preferably only establishes a communication with the client application if the client application sends a valid portal session ID to the MeDPAP controller.

Preferably, the LiSA monitors the number of client applications logged in to LiSA and therefore having or intends to have an established communication session with a MeDPAP controller of a virtual machine. In particular the login server monitors the number of virtual machines and the number of MeDPAPs running to serve the requests of client applications. In particular LiSA performs load balancing and in particular instructs a MeDPAP controller to start a new virtual machine. Thus, the MeDPAP controller is preferably constituted to receive an instruction from the login server (LiSA) to start a new virtual machine (VM) (in response to the instruction from the client application). Preferably the new virtual machine also includes a new MeDPAP controller which is constituted to start a plurality of MeDPAPs which are in particular idle MeDPAPs waiting for a communication with a client application.

As mentioned above, the MeDPAP controller is preferably constituted to respectively generate the VM session IDs for the communication sessions with the client applications so that an exclusive VM session ID is assigned to each communication session. Furthermore, the MeDPAP controller is preferably constituted to receive the above-mentioned portal session ID from the client applications. This portal session ID is preferably individual for each client application. That is, there is an exclusive unique portal session ID for each client application. The portal session ID is preferably generated by a server application. The server application is in particular a server application to which the client application logs in and is in particular the aforementioned LiSA. The portal session ID from the client application is preferably sent from the MeDPAP controller to the server application (in particular to the LiSA). Then LiSA checks whether the portal session ID is a valid portal session ID, i.e. is a portal session ID generated for one of the client applications which are currently logged in the server application (in particular the LiSA). If this is the case, the server application sends an acknowledgement, that is a confirmation that the portal session ID is okay to the MeDPAP controller. Thus, the MeDPAP controller is preferably constituted to receive the acknowledgement from the server application. The acknowledgement confirms that the portal session ID is valid or informs the MeDPAP controller that the portal session ID is not valid. In case the portal session ID is not valid, the MeDPAP controller preferably stops the communication with the client application and denies in particular any access to the MeDPAP and/or to the digital data (in particular the medical data). If the portal session ID is valid, the MeDPAP controller is preferably constituted to send the VM session ID to the client application which VM session ID is then unique for the communication with the client application.

The present invention is also directed to a data storage medium (like a DVD or hard disc or a ROM etc.) which is constituted to store digital data representing a system image of the virtual machine or an installation program for installing the components (run time) of the virtual machine, in particular for installing at least the MeDPAP controller and the executable MeDPAP on the virtual machine. According to another embodiment, a signal wave carries the information which represents the system image or the installation program. The signal wave is for instance sent by using a remote desktop protocol (RDP). The installation program includes in particular a MeDPAP controller file and a MeDPAP file to be installed.

According to a further embodiment, a method of transforming a virtual machine (which in particular does not include the software components of the previous embodiments, in particular does not include the MeDPAP controller and the MeDPAP and on which in particular an operating system is running) into the virtual machine according to one of the embodiments described above is provided. The method of transforming comprises in particular the steps of logging into the virtual machine. That is, in particular a user logs into the operation system running on the virtual machine. The user has preferably rights which allow him to load a system image of the virtual machine into the virtual machine or to install the components of the VM (in particular the MeDPAP controller and the MeDPAP) on the virtual machine. Furthermore, the method of transforming preferably comprises the step of configuring the MeDPAP controller and the MeDPAP (and optionally to configure the VM, in particular the operating system of the VM as described in the parallel application U.S. 14/000,296 described below) to be constituted to have the features as described above (or below) with respect to at least one of the embodiments of the virtual machine. That is, the MeDPAP controller and the MeDPAP are in particular constituted to perform the steps as described with respect to at least one of the above embodiments. As mentioned above, the method of transforming can in particular encompass the method of configuring the VM as described in one of the embodiments described in the parallel application.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, in particular computer-readable data storage medium comprising computer-usable, in particular computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention. Within the framework of the present invention, a computer-usable, in particular computer-readable data storage medium can be any data storage medium which can include, store, communicate, propagate or transport the program for use on or in connection with the instruction-executing system, apparatus or device. The computer-usable, in particular computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. Preferably, the data storage medium is a non-volatile data storage medium. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or vibration element incorporated into an instrument).

The invention also relates to a program which, when running on a computer or when loaded onto a computer, causes the computer to perform one or more of the transformation method steps described herein and/or to a program storage medium on which the program is stored (in particular in a non-transitory form) and/or to a computer on which the program is running or into the memory of which the program is loaded and/or to a signal wave, in particular a digital signal wave, carrying information which represents the program, in particular the aforementioned program, which in particular comprises code means which are adapted to perform any or all of the transformation method steps described herein. The program can be for instance implemented by using a macro program.

The present invention is also directed to a cloud computer system on which a virtual machine of one of the preceding embodiments is running. The cloud computer system comprises a number, in particular a plurality of computers. In particular, a plurality of the virtual machines according to one of the preceding embodiments are running on the cloud computer system. In particular, the computers (cloud computers) of the cloud computer system work as servers. Therefore, the cloud computer system is also called "cloud server farm" herein. A cloud computer is in particular a computer which is preferably accessible by the WAN.

As mentioned above, the present invention is also directed to an electronic network system. The electronic network system comprises the cloud computer system as mentioned above and at least one client computer and preferably a plurality of client computers. On the client computer a client application is running. The client computer is connected with the cloud computer system via a wide area network to exchange data with one of the MeDPAP controllers of the plurality of VMs. For exchanging the data in particular the above-mentioned controller-URI (also called VM-URI) is used to identify the MeDPAP controller which is assigned to the client application by means of the login server. That is, the login server (LS) has the login server application (LiSA) which runs on the LS and assigns the controller-URI and the aforementioned portal session ID to the client application. Both is used by the client application in order to contact the MeDPAP controller assigned to the client application. Preferably, the login server (LS), in more detail the LiSA also assigns the portal session ID to the client application and in particular sends the portal session ID to the client application so that the client application can use the portal session ID when the client applications accesses the virtual machine (in particular the MeDPAP controller). The electronic network system in particular comprises the login server (LS) which (in more detail, the LiSA of which) is configured to allow logins by the client applications; to respectively assign one of the plurality of the virtual machines to respective ones of the logged-in client applications and to respectively send the individual VM-URIs of the assigned virtual machines to the client applications; and to instruct one of the MeDPAP controllers of the plurality of virtual machines to start and/or stop the MeDPAP controller of another virtual machine in dependence on the number of logged-in client applications.

Optionally but preferably the electronic network system also comprises the login server (LS) as far as mentioned above. The login server (in more detail the LiSA) is in particular configured to allow logins from the client applications. As mentioned above, the login server (LS), in more detail the LiSA assigns a VM-URI to the client application which has logged into the login server. Preferably, the login server additionally instructs one of the MeDPAP controllers of the plurality of MeDPAP controllers running on the plurality of virtual machines to start another virtual machine if the number of client applications logged in is determined to need a further virtual machine. This determination is for instance performed if a predetermined number of clients exceeds a threshold. Correspondingly, in case one or more client application log off from LS, in more detail the LiSA, the LS, in more detail the LiSA instructs the MeDPAP controller to stop one of the running virtual machines if the number of client applications are determined to be lower than a predetermined threshold.

Preferably, LiSA instructs the MeDPAP controller only to stop one of the running machines, if none of the MeDPAPs on this one of the running virtual machines is occupied. Preferably, the LiSA memorizes (i.e. by setting a flag) one of the virtual machines to be a candidate for stopping if the number of client applications is below the predetermined threshold. In that case, no new MeDPAPs are started in the memorized one of the running virtual machines. In case all of the occupied MeDPAPs returns to an idle status in this one of the running virtual machines, then the LiSA instructs one of the MeDPAP controllers of other virtual machines to stop the one (memorized) virtual machine.

In the following, embodiments of the invention are discussed with reference to the figures, wherein FIG. 1 shows a hardware and software structure of a medical data processing system used for implementing the invention;

FIG. 2 is a functional diagram of a login procedure used for accessing the invention;

FIG. 3a is a functional diagram of an authentication procedure used during startup of the viewer;

FIG. 3b is a functional diagram of communication steps between the client application and the digital data processing application program;

FIG. 4a is a functional diagram showing the operational coupling between the client application, digital data processing application program and controller service;

FIG. 5 is a functional diagram displaying the processing of digital data; and

Figure 4B:
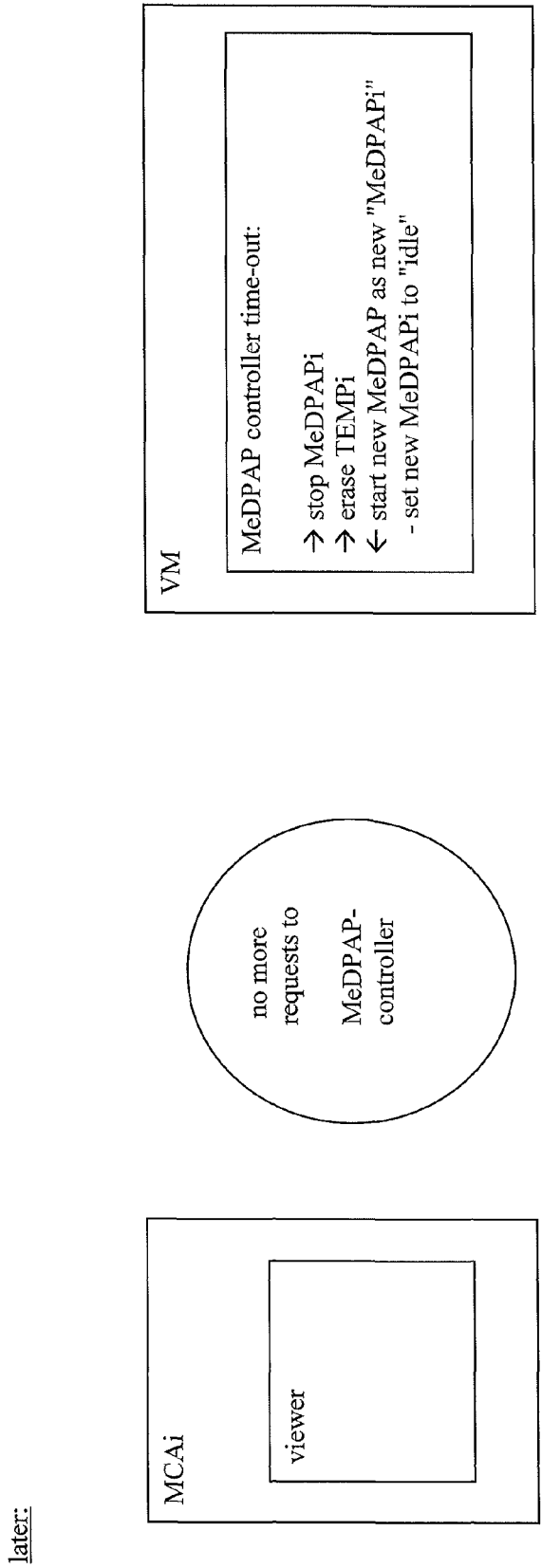
FIG. 4b is a functional diagram explaining execution of the digital data processing application program.

As shown by FIG. 1, the medical data processing system MeDProS used for implementing the invention comprises a login server LS which enables login into the medical portal application MedPort via a client computer client 1, client 2, . . . . The LS typically is a standard server computer which is accessible via the internet. The LS runs a login server application LiSA which is connected to medical client applications MCA1, MCA2, . . . via login-lines for bi-directional digital communication between the MCA and LiSA. LiSA provides a login mask as a website which is accessible via a public electronic network such as the internet (worldwide web) and is preferably programmed in a mark-up language as HTML or XML. Each client i runs MCAi, wherein i=1, . . . Y with Y denoting the total number of clients connected or connectable to LiSA. In the case of FIG. 1, Y=12. The MCA is for example an application suitable to display the contents and functionality of LiSA to a user who uses the client. For example, the MCA may be a browser application, in particular a web browser or internet browser which is a software application for retrieving, presenting and traversing information resources on a public network such as the worldwide web or another local or wide area network. The information to be represented in this case is provided by LiSA.

The LS is further operatively coupled, in particular by a data transfer line suitable for transmission of digital data, to a login server database which may take the form of a relational database. The login server database comprises user data and case IDs. The case IDs represent information describing a unique identifier of a set of patient data (also called medical case), i.e. a data set comprising in particular medical information about a patient. The user data comprise information describing the access rights of different client users and/or MCA users to specific medical cases.

A client user may be any healthcare practitioner, in particular physician, who operates the MCA and logs into LiSA by using his specific user name and password. LiSA provides an upload interface, as also called uploader, which is accessible to the client user via MCA and provides a functionality for uploading patient data to MedPort. In particular, the client user who performs such an upload operation is considered to be the owner of the medical case comprising the uploaded data. The owner is provided with a functionality to assign access rights to the medical case to other client users. For example, a client user 1, i.e. the user operating client 1 and therefore also MCA1, may open a medical case (in particular create a new medical case) and upload patient data to that medical case. MedPort will then via LiSA provide client user 1 with a graphical user interface in MCA1 which allows him to assign user rights to other client users, for example user client 2, i.e. the user operating client 2 and therefore MCA2. Such user rights may relate to the allowance to only view the patient data in an MCA and/or the allowance to download data to a client and/or the allowance to manipulate the case (for example, to remove patient data from the medical case or to change the information content of the patient data). Access rights may be user rights or owner rights. Typically, the owner has full access rights to the medical case which he owns, i.e. he is allowed to execute any functionality on the patient data or the medical case, respectively which is offered by MedPort. Such a set of user rights is also called owner rights. Access rights for a specific client user providing lower rights than owner rights are called medical case user rights.

The user data comprises information describing which user rights are assigned to a specific client user, in particular the user data also comprise information whether a client user logged into MedPort is the owner of a specific medical case. For example, the login server database comprises a table which assigns to each client user all medical cases which have been associated with that client user (i.e. all medical cases with regard to which that client user has some kind of access rights) and information about the kind of access rights which that client user has for each specific medical case. The patient data which is uploaded comprises, in particular consists of medical data, in particular medical image data and patient metadata. The patient metadata for example comprise information describing the patient's personal data such as his age, gender, body measures (such as height and other geometric dimensions and weight), information about the patient's health state (in particular information about a type of decease or injury from which the patient is suffering).

The viewer is an application, the source code of which being accessible via LiSA and stored on the cloud computer and downloadable for an MCA in order to be executed in a runtime environment plugin for MCA. For example, the viewer may be written in an application framework language suitable for being run in a runtime environment such as Microsoft® Silverlight™ or Adobe® Flash® or an environment written in HTML5. The plug-in may thus be a Silverlight™ web browser plugin or Flash® web browser plugin. The viewer comprises code which, when executed, serves as a viewing plugin for graphically displaying image data. In case a Silverlight™ plugin is used, the viewer is stored in a .xap file.

The MeDProS also comprises a virtual machine VM, which in particular is a virtual data processing machine. The VM is a simulation of a programmable machine, in particular a computer, more particularly a server. This simulation is constituted to be run on a computer, in particular a server. The virtual machine is based on a server operating system such as the Microsoft® Windows® server operating system. However, any other server operating system, for example a server operating system based on Unix and/or Linux, may be used as a basis for the virtual machine. The virtual machine in accordance with FIG. 1 is a system virtual machine which provides a complete system platform for supporting the execution of a complete operating system (OS). The virtual machine is run on a cloud computer, in particular a cloud server which is connected to the world wide web (WWW). The cloud computer on which the virtual machine is running is preferably different from the LS, in particular it is separated from the LS in terms of constituting a hardware unit of its own. However, the cloud computer and the LS are connected via a data transfer line.

On the VM, a web server, in particular an IIS-web server is installed and run. This web server executes a storage controller SC, in particular a storage service and a MeDPAP controller MC serving as the mentioned controller service, which comprises an image cache service and a load balance service. A bi-directional data transfer line called SC-checkline is established between LiSA and the SC, and a bi-directional data transfer line called MC-checkline is established between LiSA and the MC.

Furthermore, the VM comprises a VM-storage ViMStor which is a volatile memory, in particular a random-access memory RAM. On the VM, an application is installed which, when executed, simulates part of the ViMStor as a non-volatile memory, in particular as a hard disc. This non-volatile memory is in the following called RAM-disc. In the RAM-disc, different temporary storages TEMP are located for storing temporary data, which may take the form of directories which are located in the RAM-disc. In particular, the RAM-disc application is configured to generate the temporary directories in the RAM-disc.

On the VM, a medical data processing application program MeDPAP is installed. According to an embodiment of the invention, a number N of instances of MeDPAP are running on the VM, where N preferably equals 10. The number of MeDPAPs depends on the processing power of the virtual machine. The number is preferably greater than 1, in particular greater than 5 and/or lower than 50 or 100 or 1000 (or 10.000). Each instance of MeDPAP running on the VM is hereinforth also called MeDPAPi, where i=1, ..., N. Execution of each MeDPAP instance and its assignment to a specific MCAi (where i=1, N) upon request of functionalities provided by MeDPAP is controlled by the MeDPAP controller. The ViMStor comprises a number N of temporary storages TEMPi (where i=1, N). Each MeDPAPi is assigned a specific and fixed TEMPi from which the MeDPAPi may read digital data as input data for the processing conducted by MeDPAPi and to which MeDPAPi may write digital data as output data which in particular results from the data processing (in particular, image data processing) which is executed by MeDPAPi.

A number of preferably no more than N MCAi (where i=1, ..., N) is allowed to establish a connection with one VM. Each MCAi is assigned a MeDPAPi for conducting the requested data processing functionality, Once the MeDPAP controller has assigned a MeDPAPi to MCAi, a direct bi-directional communication link BiDiCoLi (where i= 1, ..., N) is established between MeDPAPi and MCAi for direct exchange of digital data between MCAi and MeDPAPi. If data processing is requested by MCAi, MCAi issues this request to MeDPAPi.

Upon a request issued by MCAi for a data processing functionality offered by MeDPAPi, MeDPAPi requests information from the storage controller SC about a storage location of the medical image data MID. The request from MCAi is connected to a specific medical case which is currently being examined by the client user using MCAi. Information about the storage locations of medical image data is stored for each medical case in the medical metadata database MeMeD which serves as the above-described patient database implemented as a relational data base service. The SC looks up the information about the storage location in MeMeD and sends this information as a reply to MeDPAPi. The reply comprises information about the storage location of the medical image data in the medical image data storage MIDaS. MeDPAPi then accesses this specific storage location in MIDaS and copies the medical image data to TEMPi. MeDPAPi then reads input image data from TEMPi and outputs the processing results as output data to TEMPi. The MeDPAP controller then sends the output image data as a processed data file ProDaF as processed medical image data via a direct data transfer line to MCAi.

A bidirectional communication line BiDiCoL is established individually and directly between each MeDPAPi assigned to an MCAi and the respective MCAi. Therefore, the individual BiDiCoL may also be abbreviated as BiDiCoLi (where i=1, ..., N). In other words, there exists a bijective mapping between the MCAis and MeDPAPis.

According to an embodiment, a number of VMs may be running on a farm of server computers (SerFa). If a predefined number of MCAi having each one BiDiCoLi with a MeDPAPi on one VM is reached, the predefined number preferably being smaller than the total number of MCAis being connectable to a MeDPAPi on a single VM (in the case of FIG. 1 denoted by VM1), a second VM, in the case of FIG. 1 denoted as VM2, is started on SerFa. SerFa is in particular a cloud computer or group of cloud computers as described above. The procedures of login, authentication, image processing and transmission of results is described for the VM and/or VM1 above then also apply to VM2 with regard to commands and requests issued from an MCAi, for example MCA12.

FIG. 2 explains a login and software transfer procedure between MCAi and LiSA. A user may login to LiSA by accessing the MedPort website, i.e. loading the MedPort website into his browser. Login to LiSA is possible via input of login data into a login mask provided to the user in the browser. The login data preferably comprise a user name and password, the password preferably being a secure password fulfilling certain criteria of combinations of characters. LiSA then generates a session ID for the session between MCAi and LiSA. The session ID is, for example, sent to a client i as data contained in a cookie. The session ID is denoted in FIG. 2 as portal session ID PSIDi for the specific i-th session of MCAi in LiSA. Together with the PSIDi, a uniform resource identifier for the VM called VM-URI is sent by LiSA to client i.

A Silverlight® plugin is downloaded to MCAi from a software distribution server and installed in the browser running on client i as a browser plugin BroPlug, if the browser does not have any such plugin already installed. The Silverlight plugin serves as a browser plugin (runtime environment) for the viewer. The viewer is also downloaded by LiSA to MCAi as a code contained in a .xap file and run in the BroPlug. In the case of FIG. 2, the viewer is written in code which is executable in a Silverlight® runtime environment. Client iBroPlug is started by accessing the viewer due to user action in MCAi. For example, if the user chooses to view image data in MCAi, the viewer is automatically activated.

Upon activating the viewer, the viewer is provided by the LiSA with a session ID (see FIG. 3a). The viewer is also provided with a VM-URI so that the viewer may establish connection to the MeDPAP controller. The MeDPAP controller then checks the access rights of the viewer and supports the communication to the viewer. The portal session ID which the viewer has previously been given is handed over by the viewer to the MeDPAP controller and the MeDPAP controller checks with the LiSA whether the portal session ID is valid. If the portal session ID is valid, the MeDPAP controller allows communication between the viewer and the MeDPAP controller. However, the viewer does not have open access to the VM (i.e. is not able to log in into the VM as a VM user) and is only allowed to issue requests to and to receive replies from predefined components (in particular services) of the VM like the MeDPAP controller. The MeDPAP controller also assigns a MeDPAPi which is currently in idle state to the viewer to support image data processing.

FIG. 3a explains the exchange of information (messages) during startup of the viewer. At the beginning, there is an authentification process during which the MCAi sends a request to the MeDPAP controller. To this end, the MCAi sends ($1^{st}$ step) the portal session ID (PSIDi) to the MeDPAP controller. In order to be able to contact the virtual machine which is assigned to the MCAi, the MCAi uses the VM-URI which the MCAi has received from LiSA. In other words, the MCAi contacts the virtual machine which has stored a unique resource identifier, the VM-URI. In more detail, the MeDPAP controller of the VM can be contacted via the WAN by using the VM-URI. After the first step, the MeDPAP controller contacts in a second step LiSA in order to ask LiSA whether the portal session ID (PSIDi) is valid or not. Assuming LiSA answers in a third step that the PSIDi is valid, then LiSA responds with an okay signal to the MeDPAP controller. If the PSIDi is not valid, the MeDPAP controller stops communication with MCAi.

According to an embodiment, the MeDPAP controller has already started execution of a plurality of MeDPAPs before the MCAi contacts the MeDPAP controller. In particular, the MeDPAP controller has assigned different URIs (MeDPAP-URIs) to the different MeDPAP instances which are running on the virtual machine in an idle state (i.e. without processing digital data) and which have been started by the MeDPAP controller. That is, for instance an URI1 (MeDPAP-URI1) has been assigned to MeDPAP1 and URI2 (MeDPAP-URI2) has been assigned to MeDPAP2 and URIi (MeDPAP-URIi) has been assigned to MeDPAPi. Furthermore, preferably the MeDPAP controller has assigned storage spaces to the different MeDPAPs which are called TEMP. In more detail, the storage space TEMP1 is assigned to MeDPAP1, the storage space TEMP2 is assigned to MeDPAP2 and the storage space TEMPi is assigned to MeDPAPi.

When the MeDPAP controller receives an okay from LiSA, the MeDPAP controller checks which one of the MeDPAPs is available, i.e. not yet assigned to another MCA. According to the example given in FIG. 3a, it is assumed that MeDPAPi is idle and available for performing processing services for MCAi. In this example, the MeDPAP controller stores the PSIDi and in particular stores an assignment between the PSIDi, the MeDPAPi and a VM-session ID which is assigned to the communication (session) between MCAi and MeDPAPi. The VM-session ID is sent from the MeDPAP controller to the MCAi (for instance in the form of a cookie). This is performed in a step 4 which also represents a confirmation that the PSIDi sent from the MCAi is valid. Sending the PSIDi to the MeDPAP controller is preferably performed by the viewer and also preferably, the viewer receives the VM-session ID which is a unique ID assigned to the communication (session) between the viewer and the MeDPAP controller.

In a next step 6, preferably the viewer of MCAi requests processing functionalities for processing digital data, in particular medical data from the MeDPAP controller (more particularly, medical image data). In other words, the MCAi asks the VM for at least one of the functionalities of the digital data processing application program (MeDPAP). The MeDPAP controller sends the URIi of the MeDPAPi (which has been assigned previously) to the viewer of the MCAi. Furthermore, preferably the MeDPAP controller changes the status of MeDPAPi from idle to occupied. That is, the MeDPAP controller is aware that MeDPAPi is no longer available in case a further MCAi contacts the MeDPAP controller and asks for the processing of digital data (i.e. asks for the functionalities of a MeDPAP). This was step number 6. In a next step number 7, the MCAi (in more detail, the viewer of MCAi) sends the PSIDi to the MeDPAPi. The MeDPAPi has a uniform resource identifier which is "URIi". Thus, the viewer contacts the address URIi in order to send PSIDi to MeDPAPi. Preferably, the MeDPAP controller has already assigned URIi to the MeDPAPi when starting the MeDPAPi. That is, preferably the URIi is assigned to MeDPAPi in a status where the MeDPAPi is still idle. In this way, the time for necessary assigning the URIi to the MeDPAPi is not spent when the MCAi needs a MeDPAPi but already before that. This decreases the response time if the MCAi asks for processing functionalities. In order to assign a URIi to the MeDPAPi, the MeDPAP controller can for instance send a string including the URIi to the MeDPAPi, in more detail to the communication service interface (CSI) of the MeDPAPi which in particular is or works as a web service, in particular a WCF web service and which in particular represents an interface to the WAN (internet). Preferably, the MeDPAPi stores the URIi and the PSIDi which it receives from the MCAi. In this way, any further requests from MCAi can be verified to be an authenticated request. This reduces the risk of producing requests of not authorized clients. To this end, in a step 8, the MeDPAPi preferably contacts the MeDPAP controller to ask whether the PSIDi is valid. The MeDPAP controller checks whether the PSIDi received from the MeDPAPi is the one which is assigned to the MeDPAPi. To this end, for instance the MeDPAP controller accesses a table in which all the assignments are stored. Then in a step 9, in case the PSIDi is valid, the MeDPAP controller sends an okay to the MeDPAPi. In response to this, the MeDPAPi preferably sends also an okay to the viewer of the MCAi and indicates to the MCAi that the MeDPAPi is ready to be used for processing of digital data. Thus, a unique relationship between one of the MCAi and one of the MeDPAPs (i.e. the MeDPAPi) is established. In particular in case of a plurality of MCAs and MeDPAPs, a bijective relationship between each of the MCAs and the occupied MeDPAPs is established, thus reducing the risk of data cross talk.

In a next step (step 11), the MCAi (in more detail the viewer of the MCAi) sends a request for processing digital data to the MeDPAPi. For instance, the MCAi sends the request to shift an image by a number of pixels (for instance n pixels). Each MeDPAPi comprises a communication service interface CSI and a digital data processing program section MDP. This request is received by the CSI of the MeDPAPi and then transferred to the digital data processing program (MDP) of the MeDPAPi. The MDP calculates the new image by shifting the pixels of the image by n pixels. The new image file generated is called "image file x.png". The MCAi preferably transfers the portal session ID together with the instruction. Before processing, the MeDPAPi preferably checks the validity of the portal session ID and processes only the data if the portal session ID is valid. Herein, the term "image file" is just an example for the file of digital data (in particular processed digital data) and in particular just an example for one or more files which include a number of images, e.g. an image or a sequence of images (for instance a stream of images) or a video sequence of images.

FIG. 4a shows the process of transfer of digital data, in more detail medical image data from the virtual machine to the MCAi. The step 11 has already been described with respect to FIG. 3b. After receiving the instruction to process the image data and after generating the file "imagefilex.png". This file is also called "ProDaF" (processed data file) in the following. The MeDPAPi translates the file name of the ProDaF ("imagefilex.png") into a Uniform Resource Identifier which is called URIx. The purpose of the URIx is to allow the MeDPAP controller to locate the ProDaF ("imagefilex.png") in the storage space (TEMPi) assigned to the MeDPAPi. To this end, the URIx can just include a translated file name of the ProDaF or can additionally include the directory path of the storage location (TEMPi). According to a preferred embodiment, the URIx just includes the translated file name and not the path and the MeDPAP controller only accesses the storage space (TEMPi) assigned to the MeDPAPi. In other words, the MeDPAP controller already knows the location of TEMPi since MeDPAPi has one defined storage space (TEMPi) and no other storage space where it stores the ProDaFs. The URIx can include as a scheme for instance HTTP and as authority for instance the IP address of the MeDPAP controller which controls the MeDPAPi and can include only optionally as a path the specification of the location of TEMPi (directory specification) and includes as a query a file name of the ProDaF.

Before or after translation of the ProDaF into URIx, the ProDaF (imagefilex.png) is stored in the TEMPi assigned to the MeDPAPi (see step 12 in FIG. 4a). In another step (called step 13), the MeDPAPi transfers the URIx to the MCAi. In this way MCAi is informed about the name of the ProDaf.

In a next step (step 14), the MCAi (in more detail the viewer) sends the URIx (and the VM session ID) to the MeDPAP controller. The MeDPAP controller has already performed an assignment between the TEMPs and the MeDPAPs. Based on the VM session ID and the assignment table, the MeDPAP controller determines the TEMPi assigned to the VM session ID and assigned to the MeDPAPi which has generated the ProDaF ("imagefilex.png"). The location of the ProDaF ("imagefilex.png") within the TEMPi is based on a retranslation of the URIx into the file name. Preferably, the MeDPAP controller is constituted to only access the TEMPi assigned to the VM session identifier in order to look for the imagefilex.png generated by the MeDPAPi. In this way, the risk of data cross talk is reduced since the MeDPAP controller is blocked to accessing other TEMPs in order to look for an image file and an erroneous retrieval of the wrong image file from other TEMPs is avoided. In order to retranslate the URIx into the file name of the ProDaF (imagefilex.png), the MeDPAP controller uses in particular the query part of the URIx.

Having located (step 15) the ProDaF within the TEMPi, the MeDPAP controller reads (step 16) the ProDaF (imagefilex.png) from the TEMPi and sends (step 17) the ProDaF (imagefilex.png) to the MCAi (in more detail to the viewer of the MCAi). The MCAi then displays the information contained in imagefilex.png to the user of the MCAi by graphical output in the viewer. Thus, there is a direct communication interaction between the MCAi and the MeDPAPi for the generation and storage of ProDaFs in a TEMPi and a direct communication interaction between the MCAi and the MeDPAP controller for the retrieval of the ProDaFs stored in the TEMPi. The link between the two direct communication interactions is established by generating the URIx which is specially suited to be handled by a browser since it can be cached. So the browser can interact with the MeDPAP controller in a usual way for retrieving images while the direct interaction between the MCAi and the MeDPAPi increases the processing speed significantly and while due to the inventive structure, the risk of data cross talk is significantly reduced.

According to an embodiment (see FIG. 4b), the MeDPAP controller has a timeout procedure according to which the MeDPAP controller monitors the time expired since the last request of the MCAi. If a predefined time has elapsed since the last request (i.e. if there is a timeout) or if the MCAi logs off (i.e. actively stops communication with the LiSA and/or the VM), then the MeDPAP controller stops the MeDPAPi assigned to the MCAi, erases the contents of TEMPi and starts a new MeDPAP instance which then is idle (i.e. not assigned to a client application). Preferably, the same URIi and TEMPi is assigned to the new and idle MeDPAPi as to the previous MeDPAPi. In order to again reduce the risk of data cross talk, the MeDPAPi is preferably constituted to erase the contents of TEMPi (to which it has access) during startup of the MeDPAPi. According to an alternative embodiment, the MeDPAP controller again erases the contents of TEMPi at startup of the new MeDPAPi. If deletion of content of TEMPi fails, then the MeDPAPi does not become available again for a communication with a client application, i.e. is blocked from being occupied b a client application.

If the MCAi logs off from LiSA, then preferably LiSA informs the VM, in particular the MeDPAP controller assigned to the MCAi and the MeDPAP controller steps the MeDPAPi.

FIG. 5 is a functional diagram for explaining the processing of the medical data and in particular the medical image data between steps 10 and 11 of FIGS. 3b and 4 regarding the request for processing digital data sent from MCAi to MeDPAPi. The viewer loads by means of the SC the accessible metadata of cases (including a case ID) to the MCAi from the LiSA. The user operating MCAi on client i selects a medical case z which is of interest to him. In a request (step a) for data processing sent from MCAi to MeDPAPi, the case ID of medical case z is transmitted from MCAi to MeDPAPi. MeDPAPi then requests from the storage controller SC the storage location for the medical data for case z. Along with this request MeDPAPi transmits the case ID for medical case z and the portal session ID to the storage controller (step b). MeDPAPi therefore transmits the PSIDi to the storage controller during execution of step b). MeDPAPi asks the SC for the location of the data of case z (step b). The storage controller then in step c) transmits the PSIDi to LiSA and requests verification from LiSA whether the PSIDi is valid. If LiSA in step d) confirms the validity of PSID to the storage controller, the storage controller then continues with step e) and sends the case ID for selecting the medical case z from MeMeD. MeMeD comprises information for each medical case describing a storage location of the corresponding medical data in MIDaS. In particular, MeMeD comprises information about a reference from each case ID to the location of the medical image data in MIDaS. In step f), the storage controller receives information about the storage location for the medical image data for medical case z. In step g), the storage controller transmits this information about the storage location to MeDPAPi. MeDPAPi then accesses MIDaS, in particular the storage location for the medical image data for medical case z in MIDaS, and copies the medical image data for case z, which in particular is raw image data, to TEMPi in order to be available as input image data for the data processing.

In accordance with one embodiment, it is also possible that more than one MCAi requests to process medical image data which is assigned to the same medical case z. This is not at last due to the fact that each MeDPAPi is uniquely assigned to each MCAi and makes use of a specific, fixed TEMPi. The raw image data contained in MIDaS are then copied by each MeDPAPi to the assigned TEMPi for individual processing according to the commands and requests issued by MCAi.

Figure 6:
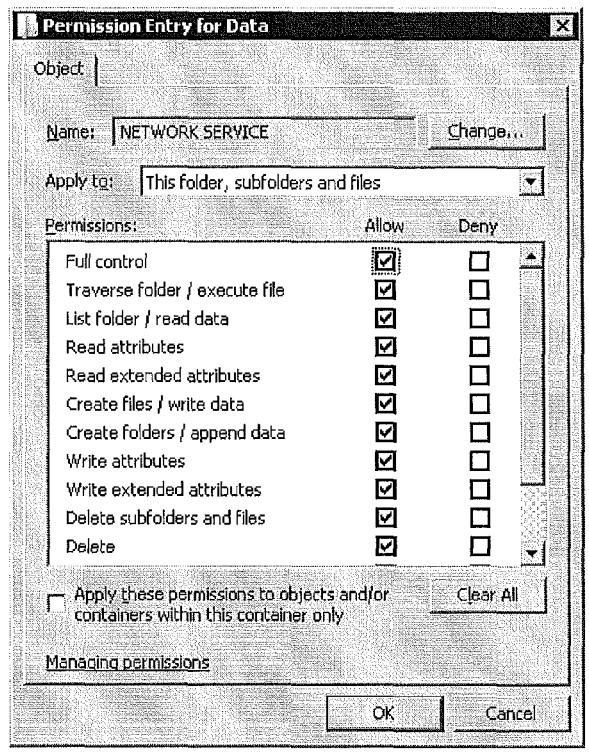
FIGS. 6a to 6f are screenshots explaining the configuration of access rights to the VM.
Figure 6:
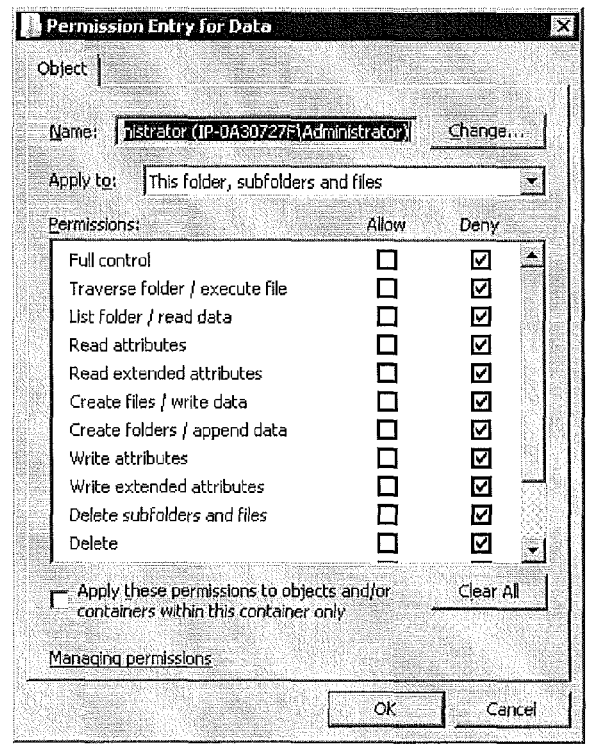
Figure 6C:
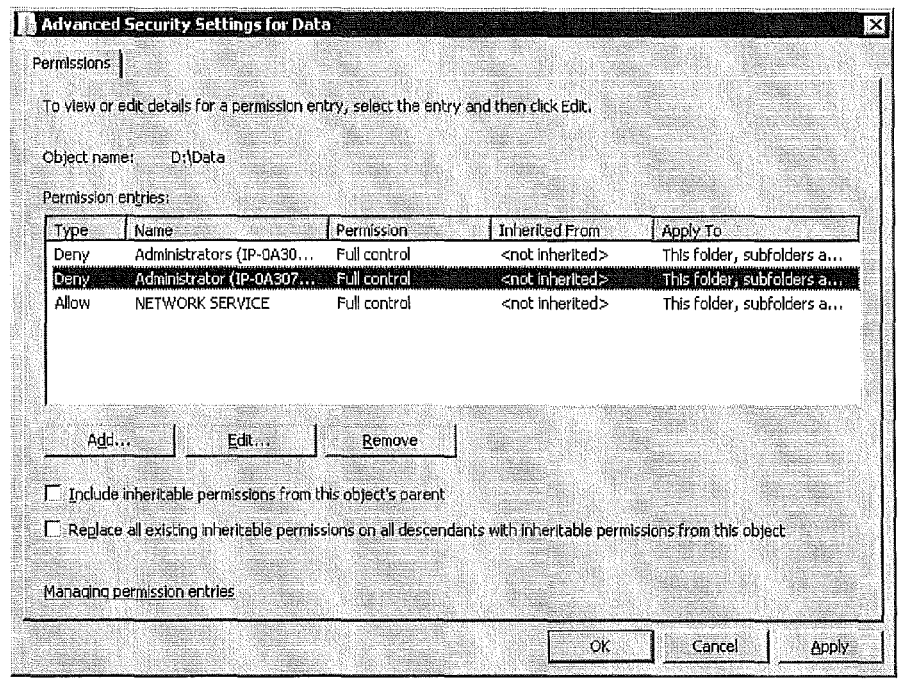

FIGS. 6a to 6c are screenshots from the Microsoft® Windows® user rights management module (URM module) and explain the configuration of user rights on the VM. The MeDPAP controller, which is the controller service for the digital processing application program as described above, is allowed at least user rights for reading, writing and deleting with regard to all of the TEMPi. This is described by FIG. 6a, wherein the MeDPAP controller is granted the rights of a network service as an example for the configuration in a Microsoft® Windows® server operating system environment. This user rights configuration for the MeDPAP controller allows the MeDPAP controller to read from and write to the TEMPi. According to FIG. 6b, the only administrator user on the VM user list is denied all permissions for all folders, i.e. all directories of the VM, this implying a complete deny of any rights to the administrator on the VM. FIG. 6c is an example for how a confirmation for the user rights set according to FIGS. 6a and 6b may be sent to the VM. When the administrator currently logged into the VM process the "OK" button shown in FIG. 6c, the changes to user rights performed according to FIGS. 6a and 6b become valid and, due to loss of all rights formerly given to the administrator, irreversible.

Figure 6D:
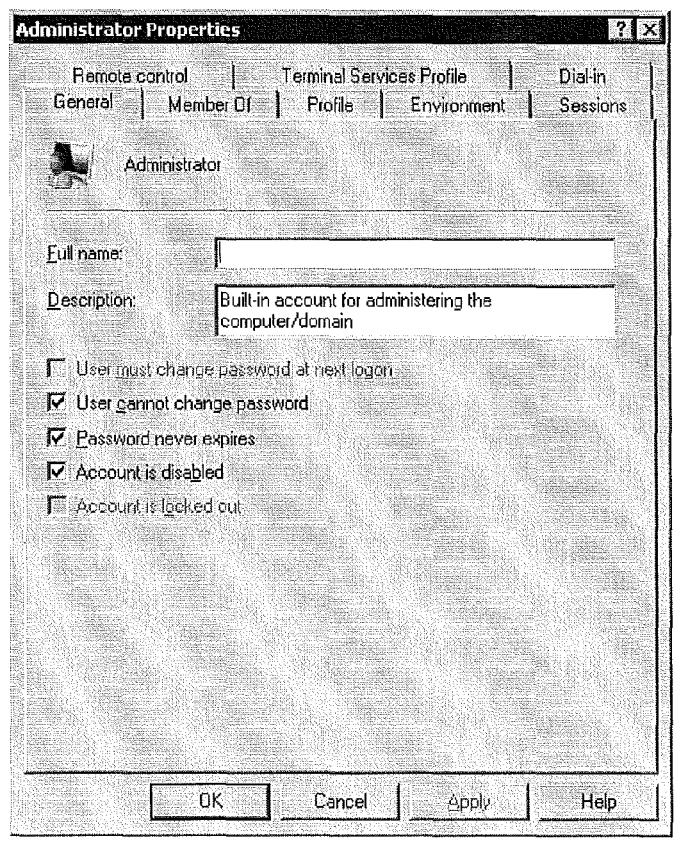
Figure 6E:
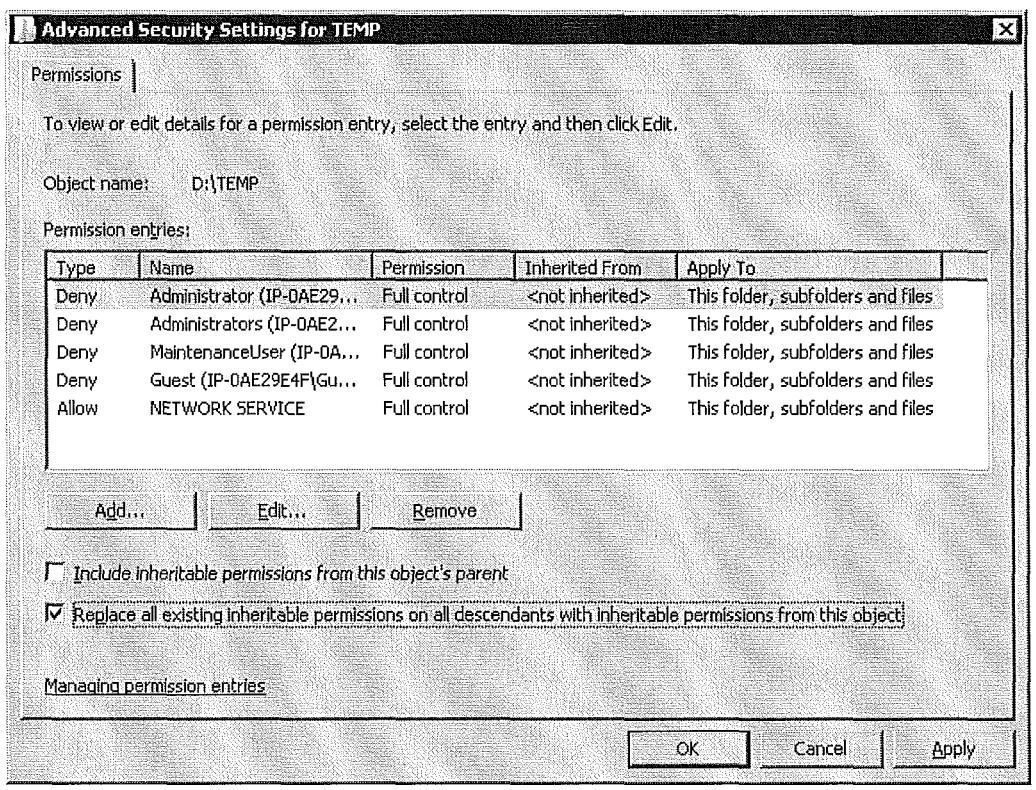

According to FIG. 6d, the administrator is deactivated by setting the option "Account is disabled", i.e. by disabling the corresponding VM user account. By applying the option marked in the screenshot shown in FIG. 6e and relating to replacing inheritable permissions, the options chosen for the administrator account are set for all members having the same rights, i.e. belonging to a group of VM users having administrator rights. The options again become valid upon selecting "OK" in FIG. 6e.

Figure 6F:
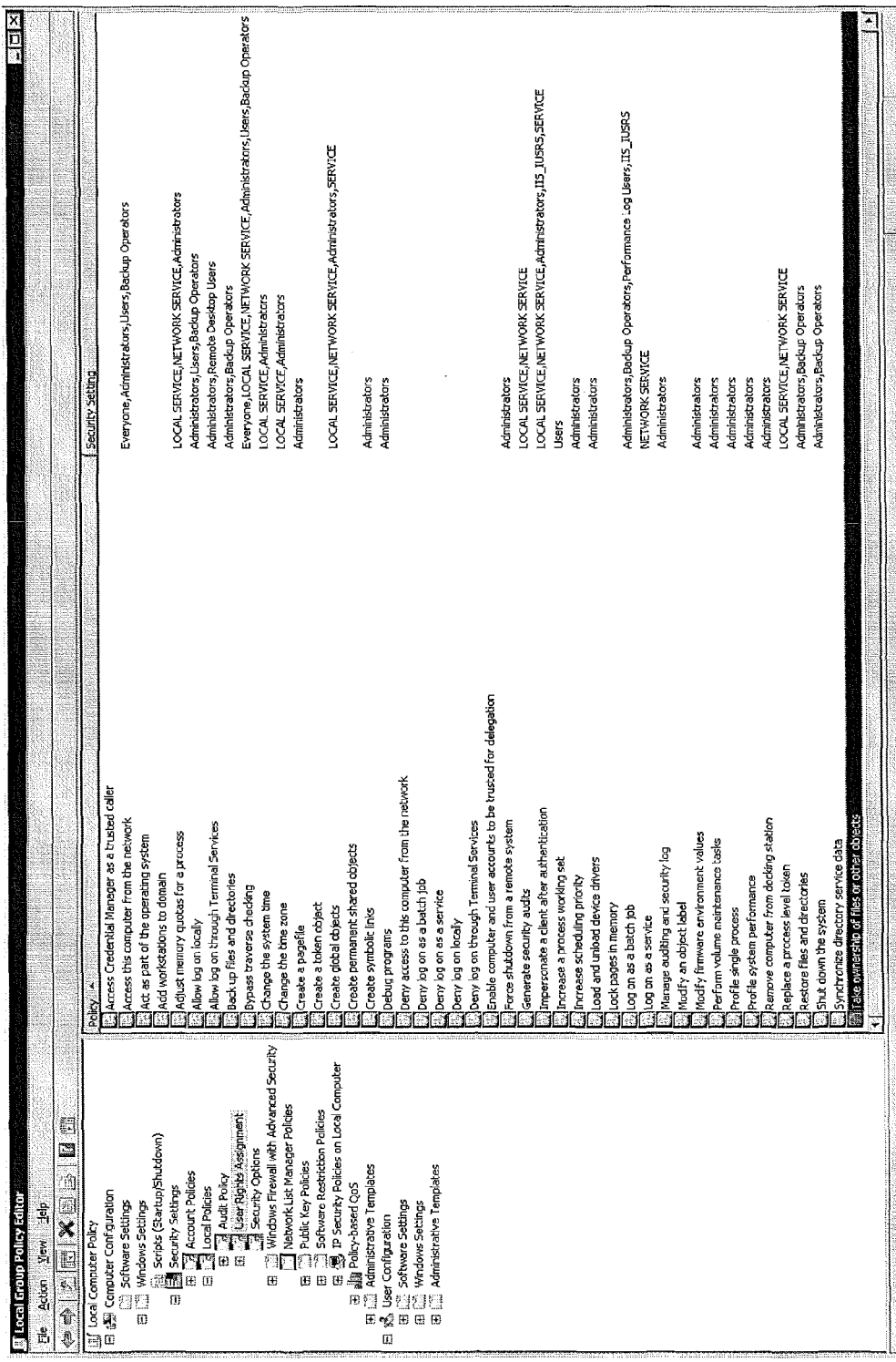

According to the screenshots from the URM module shown in FIG. 6f, no user has the right to take ownership of files or other data on the VM by setting the corresponding security setting (in particular, by choosing no VM user group) for the policy "Take ownership of files or other objects". This option therefore is valid for maintenance VM users, service VM users and VM users having basic user rights.

This invention (called MeDPAP invention) is technically related to the invention (called configuration invention) described by the patent application having the title "Virtual Machine for Processing Medical Data" U.S. 14/000,296) which in particular makes use of the virtual machine described herein and therefore offers complementary disclosure to the disclosure of this application. In particular the VM as described above optionally comprises the features of the VM as described in one of the embodiments of the parallel application. The complementary disclosure in particular includes alternative or additional features and embodiments which can be combined with the aforementioned embodiments of the MeDPAP invention. Terms used in the complementary disclosure which are identical to terms used in the above disclosure have the same meaning. The complementary disclosure of the configuration invention (also called complementary invention) is described in the following:

The complementary invention is directed to a virtual machine for processing digital data, in particular for processing medical data, by executing a digital data processing application. The complementary invention is also directed to a method of configuring the virtual machine and an electronic network comprising a computer on which the virtual machine is running.

Within the medical community, in particular the community of healthcare practitioners using medical images, it is common to discuss patient matters and to exchange data and images in order to promote patient care. So far, the relevant information has been exchanged by physical transfer of data storage media such as for example non-volatile magnetic memories or CDROMs/DVDs. This way of sharing data is, however, time-consuming and bears the risk of loss or unauthorized access.

It is therefore desirable to provide a means enabling convenient and secure transfer of patient-related data between members of a community.

US 2006/0122469 A1 discloses a medical monitoring system and corresponding method for remotely monitoring a patient. Therein, an application service provision system is accessed and a care group comprising at least one health care practitioner is defined. After assigning the patient to the care group, the members of the care group have access to patient data which is transmitted from a monitoring device which is worn by the patient. However, special needs exist in the medical community for safeguarding the confidentiality of patient-related data. That application does not address this issue.

US 2008/0006282 A1 discloses a medical imaging exchange network comprising a CT scanner and an image exchange system. A computer of the CT scanner is configured to interface with an image exchange server over a wide area network in order to make the images accessible to other authorized users' computers for review of the images.

A problem to be solved by the complementary invention therefore is to improve data security for medical data which is shared by a community.

This problem is solved by the subject-matter of any appended independent claim. Advantages, advantageous features, advantageous embodiments and advantageous aspects of the complementary invention are disclosed in the following and contained in the subject-matter of the dependent claims. Different advantageous features can be combined in accordance with the complementary invention as long as technically sensible and feasible. In particular, a feature of one embodiment which has the same or similar function of another feature of another embodiment can be exchanged with that other feature. In particular, a feature of one embodiment which supplements a further function to another embodiment can be added to the other embodiment.

Preferably, the complementary invention provides a virtual machine for processing digital data. In the following the term of virtual machine is also abbreviated as VM. Within the framework of the complementary invention, a VM is understood to be a software emulation and/or simulation of a programmable machine (in particular, a computer, more particularly a server), where the software implementation is constrained within another computer at a higher or lower level of symbolic abstraction. A VM is a software implementation of a computer which executes programs like a physical computer. Within the framework of the complementary invention, the term of virtual machine encompasses both system virtual machines and process virtual machines. A system virtual machine provides a complete system platform which supports the execution of a complete operating system (OS). A process virtual machine is designed to run a single program, i.e. it supports a single process. In principle, a virtual machine may be described in that the software running inside it is limited to the resources and abstractions provided by the virtual machine and cannot brake out of the virtual world of the virtual machine. In particular, a system virtual machine (sometimes also called hardware virtual machine) allows the sharing of the underlying physical machine resources, i.e. the resources of the physical machine (physical computer) on which the virtual machine is running, between different virtual machines, each of the virtual machines running its own operating system. The software layer providing the virtualization for the virtual machine is called a virtual machine monitor or hypervisor. A process virtual machine, sometimes also called application virtual machine, runs as a normal application inside an operating system and supports a single process. The process virtual machine is created when that process is started, and the process virtual machine is destroyed when the execution of the process is stopped or exited, respectively. The purpose of a process virtual machine is to provide a platform-independent programming infrastructure which abstracts away details of the underlying hardware or operating system on which the process virtual machine is running. Thereby, the process virtual machine allows a program to execute in the same way on any platform.

A simulation and/or or emulation of the physical computer by the virtual machine means that an emulator enables duplication of the functions of the physical computer in the virtual machine. To this end, the emulator is divided into modules that correspond in principle to the physical computer subsystem. In particular, the emulator comprises a CPU emulator or CPU simulator (the two terms being commonly used interchangeably), a memory subsystem module (which in particular is a volatile memory subsystem module for emulating a random access memory—RAM), and preferably various input/output device emulators.

As examples for an operating system used as a basis for the inventive virtual machine, a version of the Microsoft® Windows® operating system, in particular a Microsoft® Windows® server operating system, or a UNIX-type and/or LINUX-type operating system may be used. The physical computer which is simulated by the virtual machine preferably is a server computer. A server computer in particular is a physical computer which is dedicated to running at least one service in order to serve the needs of programs running on other computers (in particular so-called client computers) which are connected to the server computer within a network. The services may in particular be web services which resemble a method of communication between a client and a server within the network which in particular is an electronic network, more particularly a client-server-network. A web service may be defined as a software system designed to support interoperable machine-to-machine interaction over the network. According to the definition of the world wide web consortium (W3C), the web service has an interface described in machine-processable format (specifically, the web service description language WSDL). Other systems interact with the web service in a manner described by its description using SOAP messages, which are typically conveyed using hypertext transfer protocol (HTTP) with an extensible mark-up language (XML) serialization in conjunction with other web-related standards.

The digital data to be processed by the VM in particular is medical data. However, any other form of digital data such as scientific data input to or output from scientific simulations or other technical data comprising information about physical variables may be used as digital data. Medical data in particular is patient metadata comprising information describing personal qualities of a human being, in particular a patient, such as height, gender, geometric body dimensions (for example height, or specific dimensions of specific limbs), weight, address, workplace and physiological information such as a blood volume, tissue characteristics (for example permeability, density, elasticity) or metabolic status (for example metabolic activity, concentrations of metabolic substances such as sugar in the blood) and pathologic information such as information about a specific disease or injury from which the patient is or is expected to be suffering. The digital data may also be image data, in particular pixel data such as a data contained in a portable network graphics (PNG) format file or a joined photographic experts group (JPEG) format file or a bitmap (BMP) format file. In particular, the image data is medical image data comprising medical image information which has been acquired by using a medical imaging method and comprises image information about a patient's body region, in particular, the medical image data may comprise information representing reconstructed images (DRRs—digitally reconstructed radiographs) or a sequence of processed images (e.g. streamed content and/or a video based on medical image information). The body region may comprise soft tissue (such as an internal organ or part of the brain) or hard tissue (such as bone tissue or cartilage).

In the field of medicine, imaging methods are used to generate image data (for example, twodimensional or three-dimensional image data) of anatomical structures (such as soft tissues, bones, organs, etc.) of the human body. Medical imaging methods are understood to mean advantageously apparatus-based imaging methods (so-called medical imaging modalities and/or radiological imaging methods), such as for instance computed tomography (CT) and cone beam computed tomography (CBCT; in particular volumetric CBCT), x-ray tomography, magnetic resonance tomography (MRT or MRI), conventional x-ray, sonography and/or ultra-sound examinations, and positron emission tomography. Analytical devices are in particular used to generate the image data in apparatus-based imaging methods. The imaging methods are in particular used for medical diagnostics, to analyse the anatomical body in order to generate images which are described by the image data. The imaging methods are in particular used to detect pathological changes in the human body.

Preferably, the VM processes the digital data by executing a digital data processing application program. The digital data processing application program preferably is an executable program but may alternatively be embodied by a command line program written in a script language (hereinforth also called script). The executable program may be a program compiled from code written in an object-oriented programming language such as for example C# or C++ using the .NET framework supplied by Microsoft®. The digital data is used preferably as an input to the digital data processing application program. Preferably, the digital data processing application program is also configured to output digital data. The digital data input and/or output by the digital data processing application program in particular is medical data as described above, therefore the digital data processing application program may also be called a medical data processing application program and be abbreviated as MeDPAP. The digital data processing application program is in particular configured to have medical data, more particularly medical image data, input to the data processing algorithm which is executed by the program and also to output such data. The digital data is processed by executing the digital data processing application program preferably as an *.exe file (in particular, if meant for execution in a Windows® environment) or a file in another binary format which is executable in a UNIX/LINUX environment (for example, in the executable and linking format ELF). Execution of the digital data processing application program is then initiated by calling the program and running it on the VM, i.e. by processing it with the CPU simulator.

The volatile memory of the VM (in the following also denoted as virtual machine storage ViMStor) is represented by the memory subsystem module which preferably matches the random access memory of the physical computer. Alternatively, the volatile memory of the VM allows for advanced memory management, in which case it may be integrated into the CPU simulator. Preferably, the ViMStor is configured to comprise a storage space for temporary data (in the following also denoted TEMP) for temporarily storing the digital data. TEMP in particular takes the form of a directory or assigned memory sector in the ViMStor. Preferably, TEMP is included in a part of the ViMStor which is a simulated file system, in particular the file system of a disc drive (i.e. non-volatile memory, in particular non-volatile magnetic memory) which is simulated in the ViMStor. A file system is the structure of how data is stored and computer files are organized in particular into database for storage, organization and manipulation and retrieval by the operating system of a computer. Parts of this structure in particular are directories. This concept of simulating a file system is known as RAM disk or RAM drive. To this end, the virtual machine is generically configured such that part of the ViMStor is reserved for TEMP. The TEMP then is addressed just as a physical hard drive would be addressed. Preferably, TEMP is used for storing the digital data temporarily while it is accessed (i.e. read or written) by the digital data processing application program during processing of the digital data. The storage space for temporary data is used to temporarily store the input digital data and preferably also to temporarily store the output digital data. An advantage of employing the RAM disk concept for TEMP is that the data stored on TEMP is protected from unauthorized access. In particular, if the RAM disk, more particularly the RAM disk application which is used for simulating the file system, is stopped or the power supply to the underlying physical computer is cut, the contents of TEMP instantaneously becomes inaccessible, in particular is deleted. Among other advantages of this concept is the advantage that, even if the underlying physical computer is booted with for example a boot disc, the person doing so is not able to read the data stored in TEMP which would be the case if, for example, the data were stored in a permanent memory of the underlying physical computer.

Preferably, the VM is configured to be accessed by any virtual machine user activated on a virtual machine user list (hereinforth abbreviated as VM user list). The VM preferably is based on an operation system which supports user rights management which may be implemented as a user rights management module (URM module), i.e. the VM preferably is a multiuser machine. The URM module comprises the VM user list which is preferably preconfigured in a system image for the VM. The VM user list comprises, in particular consists of a group of maintenance VM users and a group of service VM users (being a group of technical VM users as described below). The group of maintenance VM users comprises, in particular consists of users having administrator rights (its members in the following also called administrator or system operator—SysOp) and a group of monitoring users having basic user rights. Administrator rights generally comprise the right to install programs on the operating system and to configure the operating system. More particularly, administrator rights also comprise the right to edit the VM user list, in detail to manage the rights given to a specific VM user on the VM user list and/or to add or remove VM users to and/or from the VM user list. Preferably, these rights are not granted to VM users having basic user rights.

The URM module provides options for activating or deactivating a VM user on the VM user list which may be done by setting or removing a specific option for the respective VM user account (i.e. the entry in the VM user list corresponding to that specific VM user). A user account is an entry into the VM user list for a specific user who is assigned to a group of VM users depending on the rights of that group of VM users which he shall share. A VM user account allows a VM user to authenticate to VM system services and be granted authorization to access those services. To login to a VM user account, that specific VM user to whom this VM user account is assigned is typically required to authenticate himself with his user name and his password for the purposes for in particular accounting, security, login and resource management. If a VM user account has been deactivated on the VM user list, the VM user associated with that VM user account may no longer access the VM or operate on it. Deactivation of the user account (and therefore of the VM user to whom that VM user account is assigned) is performed by opening the URM module and setting corresponding options for the specific VM user account. The deactivation becomes valid and/or enters into force when a specific action is performed on the VM, for example if a confirmation command is issued to the VM or preferably at the latest when the VM user who performed the deactivation logs off from the VM. Alternatively, deactivating may be conducted by removing the user account from the VM user list.

Another member of the group of maintenance VM users preferably is a monitoring user. The VM user account assigned to the monitoring user may, for example, be used by the manufacturer or maintenance operator of the VM to login to the VM and view monitoring data comprising information about the activity of the VM such as for example information contained in log files. Such monitoring information may, for example, describe the computing activity of the CPU module or tasks performed by the digital data processing application program. The monitoring user is preferably assigned basic user rights but not administrator rights. Preferably, the monitoring user (in particular, the monitoring user's account) is activated on the VM user list. Therefore, the monitoring user is allowed to access the VM, for example, by means of remote login via an electronic network such as a local area network (LAN) or wide area network (WAN). Access to the VM is preferably granted via a login module of the VM which provides a login mask which allows for input of the VM user name, in particular the monitoring users' user name, and the password assigned to that VM user name.

Preferably, any maintenance VM user (in particular, all maintenance VM users) who is activated on the VM user list (in particular, by activating his user account) is denied any permission regarding TEMP, i.e. has no right to perform any possible operation on or with TEMP. Alternatively all access rights are removed from TEMP from all users except the technical service user. In particular, no activated maintenance VM user is allowed (i.e. has the rights) to perform a reading, writing, copying or deleting operation on the storage space for temporary data. Denying the permissions preferably also encompasses denying the permissions for conducting any other modification to TEMP, in particular creating, copying, moving or deleting TEMP itself. Denying the permissions is preferably performed by logging into to the VM as an administrator, i.e. by using an administrator account, and setting corresponding options for the storage space for temporary data for each maintenance VM user in the URM module. In particular, denying any permissions regarding TEMP also comprises denying any permission regarding TEMP for any administrator on the VM user list. Since the monitoring user also is a member of the group of maintenance VM users, also his permissions regarding TEMP are preferably denied.

Preferably, any administrator (in particular, all administrators listed on the VM user list) has been deactivated on the VM user list. Preferably, deactivating any administrator is conducted after denying the permission regarding the storage space for temporary data. Deactivating any administrator is preferably performed by logging into the VM as an administrator as described above and setting and/or removing corresponding options for each administrator in account the VM user list. Deactivating a user account means that the user account remains in the VM user list but its use is disabled. Alternatively, deactivating may be done by removing the user account from the VM user list. As above, this is preferably done by accessing the URM module and setting corresponding options. Preferably, the monitoring user is not an administrator, i.e. does not have administrator rights on the VM. Therefore, the monitoring user is preferably not deactivated such that he has the necessary rights to perform his monitoring actions, in particular remains able to access the VM (in particular, by login) and operate on it. Preferably, any guest user on the VM user list is deactivated in the same manner as any administrator is deactivated.

Preferably, the VM is in a state in which the administrator has logged off. This specific administrator in particular is the administrator under whose VM user account any administrator was deactivated. More preferably, logging of the administrator is performed after deactivating any administrator on the VM user list. Thereby, no user belonging to the group of VM users having administrator rights (hereinforth also called administrator group) can log in into the VM after the logoff operation. In particular, the VM users belonging to the administrator group is locked out of the VM even though his user account continues to exist on the VM user list. In particular, deactivating any administrator on the VM user list leads to a preferably complete inability to use any administrator account after logging off.

Preferably, the VM is configured to allow at least one service user on the VM user list to execute the digital data processing application program and to access TEMP. The at least one service user preferably is a technical user, i.e. a system service user context, whose user account or user context, respectively, does not offer any possibility of login into the VM. This at least one service user preferably has basic user rights on the VM, in particular the service user has no rights allowing to change and/or continue user rights or to install any software, in particular application, on the VM. In particular, at least one service user is activated on the VM user list and has reading, writing and deleting rights on TEMP. In contrast thereto, no maintenance user on the VM user list has the rights to take ownership of TEMP or to install software on the VM or to start software on the VM in the user context of the service user (i.e. by using the user context of the service user). The digital data processing application program is preferably executed (in particular called) by the at least one service user, in particular by using the services user's rights. In particular, the digital data processing application program is executed such that it has the rights regarding TEMP which are assigned to the service user, in particular for reading input digital data from TEMP and writing output digital data to TEMP. A service within the context of the complementary invention is understood to be in particular a network service. A network service is an abstracted function which is provided to users or clients, respectively, in a computing network. A network service is a self-contained functional component which may be realized using one or more network protocols. An example of a network service is the world wide web which provides the internet. The internet is technically realized by the network protocol hypertext transfer protocol (HTTP). A service may also be described as a computer program that runs in the background rather than under the direct control of a user. Usually, a service is initiated as a background process. Within the framework of the complementary invention, a service user is understood to be preferably a service who is assigned a VM user account on the VM user list in order to define the user rights which that service has when running on the VM and conducting certain operations. Preferably, at least one such service user is allowed to execute, i.e. to call and run the digital data processing application program. This at least one service user preferably is assigned to a controller (i.e. a controller service) for in particular controlling initiation and exit of execution of the digital data processing application program. This controller is also called medical data processing application program controller (MeDPAP controller or MC). The controller is also allowed to access TEMP, in particular to read digital data from TEMP and to write digital data to TEMP.

Preferably, the VM is present (in particular, run) on a cloud computer, in particular a cloud server. More preferably, the VM is present on a cloud computer system which in particular denotes a system of at least one cloud computer, in particular plural operatively interconnected cloud computers such as a server farm SerFa. Preferably, the cloud computer is connected to a wide area network such as the world wide web (WWW). Such a cloud computer is located in a so-called cloud of computers which are all connected to the world wide web. Such an infrastructure is used for cloud computing which describes computation, software, data access and storage services that do not require end-user knowledge of physical location and configuration of the computer that delivers a specific service. In particular, the term "cloud" is used as a metaphor for the internet (world wide web). In particular, the cloud provides computing infrastructure as a service (IaaS). The cloud computer functions as a virtual host for the VM. Preferably, the cloud computer is an elastic compute cloud (EC2) provided by Amazon Web Services™.

Preferably, the VM is configured to read patient metadata from a patient database and to read medical image data from an image data storage device. To this end, the VM is connectable to a digital data storage device comprising a relational database in which the patient metadata is stored. This relational database is also called patient database. The image data storage device is a file storage such as a simple storage service (S3) provided by Amazon Web Service™ which is a key-value-based file hosting service. S3 provides storage through a simple web service interface and its design is aimed at providing scalability, high availability and low latency at commodity posts. Data stored in the S3 is organized in so-called buckets. Each bucket has a unique identifier within the data processing infrastructure used for implementing the complementary invention. In particular, its name may occur only once within this infrastructure. The data are organized in buckets by way of the file name of the file in which the data is saved. The file name has to be unique per bucket.

Preferably, the contents of TEMP is determined when execution of the digital data processing application is initiated, in particular, when the application starts to run. Preferably, determining the contents of TEMP means to determine whether TEMP contains any data without limitation to the kind of contents which the data represents. Determining the contents preferably is performed by the controller of the digital data processing application program or the digital data processing application program itself. In particular, the digital data processing application program may contain executable or script code which contains commands to determine the contents of TEMP. Determining the contents in particular leads to the result of contents either being present or not present in TEMP. Preferably, if it is determined that TEMP is not empty, the contents of TEMP is removed, in particular deleted. TEMP being not empty in particular means that there is some data present, in particular stored, in TEMP. The action of deleting is again performed by preferably the digital data processing application or by its controller by executing a corresponding command.

Preferably, a predefined number, in particular ten, of instances of the digital data processing application program are running or ready to run on the VM and await assignment to an application running on a client computer and accessing the VM (in particular, by communicating with a web server of the VM) via a login server (which will be described further below) and the controller of the digital data processing application program. An instance being ready to run in particular means that the digital data processing application program is contained in the VM (in particular, installed on the VM) but has not been started in order to generate an instance. Preferably, the predefined number of instances depends on the performance and/or hardware capability of the underlying physical computer. Preferably, the digital data processing application program is present as a file only once on the VM. An instance of the digital data processing application program is the running digital data processing application program. In particular the digital data processing application program may be executed more than once simultaneously on the VM. Preferably, a plurality of instances of the digital data processing application program is running while the VM is running. These instances then initially are in an idle state, i.e. they are not processing digital data which in particular means they are neither reading input digital data nor outputting output digital data. Each client application is assigned one idle instance of the digital data processing application program in case its functionality is requested by the client application. This in particular is the case if the client application requests to have data processed in a manner which is supported by the digital data processing application program. The controller service assigns the specific client application requesting such a functionality to a specific one of the instances of the digital data processing application program. The instance then changes to an occupied state. The controller service preferably transmits address information (in particular, a uniform resource identifier) of the instance to the client application such that the client application may communicate directly with the instance within a session. As long as the session is established, the controller service receives a connection signal, in particular a ping, from each client currently being assigned to a digital data processing application program instance. Such a connection signal is requested by the controller service and received from each of the clients at preferably predefined intervals in order to monitor the session time. If no connection signal is received by the controller service within such an interval, it is determined (in particular, by the controller service) that the session has been exited (in particular exited by the client), i.e. the session has finished. In that case, the assignment between the digital data processing application program instance and the client application is cancelled and that specific instance is stopped and restarted by the controller service and then remains running in an idle state on the VM in order to be available for assignment to another or the same client application program upon request. If the controller service determines that the session is finished, the controller service removes, in particular deletes, the contents of TEMP, i.e. preferably any data contained in TEMP. The digital data processing application program is allowed (in particular, by the controller service) to accept a new assignment only if it is determined (in particular, by the controller service) that TEMP is empty.

Preferably, any of the above-described deleting operations is conducted in a safe manner such that the data which have been deleted may not be reconstructed. Such a safe deletion may be implemented by overwriting the respective sectors of TEMP from which data has been deleted with an arbitrary, preferably statistically generated sequence of bits.

The complementary invention also relates to embodiments of the VM as described below and by the complementary disclosure of the technically related patent application (U.S. 14/001,289) defined later:

The virtual machine (VM) preferably comprises at least one of the following components and/or features:
 a MeDPAP controller (MC) which is preferably constituted
  so that it can be addressed by a Uniform Resource Identifier called VM-URI via a wide area network (WAN), and
  to supports direct interoperable interaction with a client application (MCA) over the wide area network (WAN),
  to assign a Uniform Resource Identifier called MeDPAP-URI to the MeDPAP, and
  to send the assigned MeDPAP-URI to the client application via the wide area network (WAN); and
 preferably the MeDPAP which is preferably (optionally) constituted
  to process the digital data (MD),
  so that it can be addressed by the client application via the wide area network (WAN) by using the MeDPAP-URI, and
  to support direct interaction with the client application over the wide area network for receiving instructions from the client application (MCA) to process the digital data; and/or
 wherein the MeDPAP is preferably (optionally) constituted
  to store a file (Prodaf) of the processed digital data called Prodaf in a storage space,
  to translate a location of the Prodaf into an individual Unique Resource Identifier called Prodaf-URI (URIx), and
  to send the Prodaf-URI (URIx) to the client application via the wide area network (WAN); and/or
 wherein the MeDPAP controller is preferably (optionally) constituted
  to re-translate the Prodaf-URI (URIx) received from the client application via the wide area network (WAN) into the location of the Prodaf,
  to read the Prodaf by using the re-translated storage location, and to send the Prodaf to the client application (MCA) via the wide area network (WAN),
 wherein the virtual machine is preferably (optionally) constituted so that a plurality of the MeDPAPs can be executed on the virtual machine (VM); and
 wherein the MeDPAP controller is preferably (optionally) constituted
  to respectively assign individual MeDPAP-URIs (URIi) to the MeDPAPs and to store the respective assignment between the MeDPAP-URIs and MeDPAPs,
  to be addressable by a plurality of the client applications via the wide area network (WAN) by using the VM-URI, to respectively assign one of the MeDPAP-URIs (URIi) to one of the MeDPAPs, and to respectively send the assigned MeDPAP-URIs to the assigned client applications;

wherein the MeDPAP is preferably (optionally) constituted so that if the plurality of MeDPAPs are executed on the VM, the MeDPAPs can be respectively addressed by one of the plurality of the client applications via the wide area network (WAN) by using the sent and assigned individual MeDPAP-URI (URIi) and respectively support direct interaction with the client applications over the wide area network (WAN) for receiving instructions from the client applications to process the digital data.

The complementary invention is also directed to a data storage medium comprising system image data comprising information which describes a system image of the VM and/or installation data for installing at least parts of the VM (comprising preferably at least one digital data processing application program), in particular for installing at least one component of the VM on the VM. In case the data storage medium comprises only the installation data, preferably the data storage medium does not comprise installation data for installing an operating system of the VM. In that case, the installation data preferably contains only data for installing at least one component. The term of component in particular encompasses the digital data processing application program, the web server (comprising preferably a storage controller and/or the controller service) and an application for generating TEMP, in particular a RAM disk application. A system image is a copy of the entire state of the VM, in particular in a state stored in a file on a non-volatile data storage medium (such as a permanent magnetic memory or an optical storage medium such as a DVD or CD-ROM). The system image of the VM preferably is a disc image which contains the complete contents and structure representing the VM, in particular comprising data describing information about the VM operating system and any software, in particular application programs such as the digital data processing application program, installed on the VM. Preferably, the system image is stored in an ISO-compatible format or universal disc format (UDF). The system image may be used for backup or cloning, i.e. replication, of the VM. Replication of the VM is preferably done by loading its source code, i.e. copying its system image, onto the underlying physical computer (in particular, into its non-volatile memory), and by preferably running the VM on that computer.

As a further part of the complementary invention, an electronic network system comprising a cloud computer and a login server is described. The electronic network system is in particular a system of computers which is configured to be connected to a computer network, i.e. a collection of computers and devices connected by communication channels that facilitate communications among users and allow users to share resources. An example of such a computer network may be any local network area (LAN) or wide area network (WAN) such as for example the internet (world wide web—WWW), in particular any client-server network. The electronic network system is a system of computers (i.e. a system of interconnected servers and/or clients) which is configured to be connected to such an electronic network. The cloud computer preferably is the cloud computer on which the VM as described above is running. The cloud computer is preferably connected to the patient database comprising the patient metadata and the image storage device comprising image data, in particular medical image data as described above. The login server preferably is a standard server computer which enables login to a preferably HTML-based portal application from a client computer, the portal application being able to communicate and/or access the VM via requests sent to the web server. The login server is preferably connected to the cloud computer and a login server database. The login server database preferably comprises information about the client user who has logged into the portal application. This information about the client user is preferably associated with access rights information describing access rights to the patient nietadata and the image data, in particular medical image data. In particular, the access rights information is associated with the client user. More particularly, the login server database provides a list of access rights to specific medical cases which have been assigned to the client user logged into the portal application either because he is the owner of the medical case or the owner has granted access rights to the client user. The access rights may for example be to read (view) and/or write (copy) and/or manipulate (in particular, to process) the patient metadata and/or medical image data.

Login into the portal application is preferably provided by a login mask provided by the in particular HTML-based software or code which is used to make the portal application accessible to client users. Preferably, the portal application is configured to connect medical users being members of a medical user group with one another. Medical users may be any healthcare practitioners such as physicians, nurses, psychotherapists or paramedics. A Medical user group in particular is a set of medical users, more particularly medical users who have connections to one another. The connections may be personal, in particular real-life acquaintances, and/or connections of a virtual kind achieved by establishing a contact within the portal application. The portal application preferably is a kind of social network or community network which allows a user to establish contact with other users by for example using a messaging function provided by the portal application. The messaging function may for example be a sub-program configured to send digital messages such as emails to the portal accounts of other users or text messages to mobile phones. Alternatively or additionally, the portal application preferably provides a module for establishing voice-over-IP (VoIP) contact between users. The portal is designed to connect the medical users with one another in order to enable transfer of medical data, in particular medical image data between them. The transfer of the medical data is preferably enabled by providing access possibilities to medical cases comprising the specific medical data to different client users, in particular medical users. It is assumed that a specific medical user creates a medical case for a specific patient and uploads medical data which is saved in the patient database (in the case of patient metadata) and image storage device (in the case of image data). The medical data is assigned to the medical case and the medical user who initially uploads the medical data is called the owner of the medical data and the medical case. The owner has full rights regarding the medical case and the medical data, in particular he is allowed to upload, read, download, manipulate and delete the medical case and/or the medical data. The owner is also able to assign the respective rights to other users or to remove rights for other users which he had previously assigned. In particular, access rights for members of the medical user group to a patient dataset, i.e. a medical case, are therefore controlled by the owner. Transfer of the medical data between different medical users in particular denotes an exchange of the information contained in the medical data, in particular allowing different medical users to read the information represented by the medical data.

Preferably, deleting the medical case, in particular the patient dataset, i.e. the patient metadata and/or the medical image data, from the patient database and/or the image storage device, respectively, has the consequence that no client user can access the patient dataset anymore. In particular, deleting the patient dataset is final and may not be reversed and/or undone. Preferably, deleting the patient dataset means that the patient dataset is completely removed from the respective storage facilities without being moved to an intermediate storage such a recycling bin where it could await final deletion. Preferably, deleting the patient dataset is a safe deletion procedure, which in particular encompasses overwriting the physical memory used for storage of the patient dataset with an arbitrary, in particular statistically generated, pattern.

A further part of the complementary invention is disclosed as a method of configuring the above-described virtual machine. The method comprises steps which support achieving the configuration of the virtual machine as described above.

Within the framework of the complementary invention, computer program elements can be embodied by hardware and/or software (this includes firmware, resident software, micro-code, etc.). Within the framework of the complementary invention, computer program elements can take the form of a computer program product which can be embodied by a computer-usable, in particular computer-readable data storage medium comprising computer-usable, in particular computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the complementary invention. Within the framework of the complementary invention, a computer-usable, in particular computer-readable data storage medium can be any data storage medium which can include, store, communicate, propagate or transport the program for use on or in connection with the instruction-executing system, apparatus or device. The computer-usable, in particular computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. Preferably, the data storage medium is a non-volatile data storage medium. The computer program product and any software and/or hardware described here form the various means for performing the functions of the complementary invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or vibration element incorporated into an instrument).

The method of configuring in accordance with the complementary invention is in particular a data processing method which is preferably embodied by a computer program. The data processing method is preferably performed using technical means, in particular a computer. The computer in particular comprises a processor and a memory in order to process the data, in particular electronically and/or optically. The calculating steps, in particular configuring steps, more particularly option setting steps described are in particular performed by a computer. A computer is in particular any kind of data processing device, in particular electronic data processing device. A computer can be a device which is generally thought of as such, for example desktop PCs, notebooks, netbooks, etc., but can also be any programmable apparatus, such as for example a mobile phone or an embedded processor. A computer can in particular comprise a system (network) of "sub-computers", wherein each sub-computer represents a computer in its own right. A computer in particular comprises interfaces in order to receive or output data and/or perform an analogue-to-digital conversion. A computer may also be part of an electronic network such as a client-server network. Thus, the term of computer encompasses both a client and a server.

The complementary invention therefore is also directed to a program, which, when running on a computer or when loaded onto a computer, causes the computer to perform one or more the method steps of the method of configuring the virtual machine. Use of such a program includes automatic configuration of the virtual machine, in particular to enable automatic extraction and installation of software, preferably from the system image of the VM, in order to install the virtual machine on a physical computer.

The complementary invention also relates to a data storage medium, in particular program storage medium on which the program is stored (in particular in a non-transitory form) and/or to a computer on which the program is running or into the memory of which the program is loaded and/or to a signal wave, in particular a digital signal wave, carrying information which represents the program, in particular the aforementioned program, which in particular comprises code means which are adapted to perform any or all of the method steps described herein.

The complementary invention is in particular directed to the following embodiments. Each of the following embodiments can be combined with an embodiment of the MeDPAP invention.

A) A virtual machine (VM) for processing digital data, in particular medical data, by executing a digital data processing application program, in particular a medical data processing application program (MeDPAP), the virtual machine (VM) being a simulation of a computer and in particular being the VM as described by one of the embodiments of the MeDPAP invention,
  a) the virtual machine (VM) comprising a volatile memory (ViMStor) configured to comprise a storage space for temporary data (TEMP) for temporarily storing the digital data;
  b) the virtual machine (VM) being configured to be accessed by, any virtual machine user activated on a virtual machine user list, wherein any activated maintenance virtual machine user is denied any permission regarding the storage space for temporary data (TEMP), wherein denying any permissions is performed by logging into the virtual machine (VM) as an administrator and setting corresponding options;

c) wherein any administrator has been deactivated on the virtual machine user list, wherein deactivating any administrator has been performed by logging into the virtual machine (VM) as an administrator and setting corresponding options for each administrator in the virtual machine user list;

d) wherein the virtual machine (VM) is in a state in which the administrator has been logged off after deactivating the administrator on the virtual machine user list.

B) The virtual machine (VM) according to the preceding embodiment and/or according to one of the embodiments of the MeDPAP invention, wherein the virtual machine (VM) is configured to allow at least one service user on the virtual machine user list to execute the digital data processing application program and to access the storage space for temporary data (TEMP).

C) The virtual machine (VM) according to the preceding embodiment and/or according to one of the embodiments of the MeDPAP invention, wherein the virtual machine (VM) is present on a cloud computer system.

D) The virtual machine (VM) according to any one of the preceding embodiments and/or according to one of the embodiments of the MeDPAP invention, wherein the storage space for temporary data (TEMP) is a file system, in particular a file system of a non-volatile memory, simulated in the volatile memory (ViMStor).

E) The virtual machine (VM) according to any one of the preceding embodiments and/or according to one of the embodiments of the MeDPAP invention, comprising at least the following components:

a MeDPAP controller (MC) which is constituted
so that it can be addressed by a Uniform Resource Identifier called VM-URI via a wide area network (WAN), and
to supports direct interoperable interaction with a client application (MCA) over the wide area network (WAN),
to assign a Uniform Resource Identifier called MeD-PAP-URI to the MeDPAP, and
to send the assigned MeDPAP-URI to the client application via the wide area network (WAN); and the MeDPAP which is constituted
to process the digital data (MD),
so that it can be addressed by the client application via the wide area network (WAN) by using the MeD-PAP-URI, and
to support direct interaction with the client application over the wide area network for receiving instructions from the client application (MCA) to process the digital data
wherein the MeDPAP is constituted
to store a file (Prodaf) of the processed digital data called Prodaf in a storage space,
to translate a location of the Prodaf into an individual Unique Resource Identifier called Prodaf-URI (URIx), and
to send the Prodaf-URI (URIx) to the client application via the wide area network (WAN);

wherein the MeDPAP controller is constituted
to re-translate the Prodaf-URI (URIx) received from the client application via the wide area network (WAN) into the location of the Prodaf,
to read the Prodaf by using the re-translated storage location, and to send the Prodaf to the client application (MCA) via the wide area network (WAN), wherein the virtual machine is constituted so that a plurality of the MeDPAPs can be executed on the virtual machine (VM); and wherein the MeDPAP controller is constituted
to respectively assign individual MeDPAP-URIs (URIi) to the MeDPAPs and to store the respective assignment between the MeDPAP-URIs and MeD-PAPs,
to be addressable by a plurality of the client applications via the wide area network (WAN) by using the VM-URI,
to respectively assign one of the MeDPAP-URIs (URIi) to one of the MeDPAPs, and
to respectively send the assigned MeDPAP-URIs to the assigned client applications;

wherein the MeDPAP is constituted so that if the plurality of MeDPAPs are executed on the VM, the MeDPAPs can be respectively addressed by one of the plurality of the client applications via the wide area network (WAN) by using the sent and assigned individual MeDPAP-URI (URIi) and respectively support direct interaction with the client applications over the wide area network (WAN) for receiving instructions from the client applications to process the digital data.

F) The virtual machine (VM) according to any one of the preceding embodiments and/or according to one of the embodiments of the MeDPAP invention, wherein the virtual machine (VM) is configured to read patient metadata from a patient database (MeMeD) and to read medical image data from an image data storage device (MIDaS).

G) The virtual machine (VM) according to any one of the preceding embodiment and/or according to one of the embodiments of the MeDPAP invention, wherein, when execution of the digital data processing application is called, the contents of the storage space for temporary data (TEMP) is determined and wherein preferably, if it is determined that the storage space for temporary data (TEMP) is not empty, the contents of the storage space for temporary data (TEMP) is deleted.

H) A data storage medium comprising system image data comprising information describing a system image of the virtual machine (VM) according to any one of the preceding embodiments and/or according to one of the embodiments of the MeDPAP invention or installation data for installing at least one component of the virtual machine (VM) according to any one of the preceding embodiments and/or according to one of the embodiments of the MeDPAP invention on the virtual machine (VM) according to any one of the preceding embodiments.

I) A computer on which the virtual machine (VM) according to any one of the preceding virtual machine embodiments and/or according to one of the embodiments of the MeDPAP invention is running.

J) An electronic network system comprising:
a cloud computer system on which the virtual machine (VM) according to any one of the preceding virtual machine embodiment and/or according to one of the embodiments of the MeDPAP invention is running and which cloud computer is connected to a patient database (MeMeD) comprising patient metadata and an image storage device (MIDaS) comprising medical image data;
a login server (LS) which enables login of a client user from a client computer (Client) and is connected to the cloud computer system and a login server database comprising information about the client user associated with access rights information describing access rights to the patient metadata and the medical image data.

K) The electronic network according to the preceding embodiment and/or according to one of the embodiments of the MeDPAP invention, wherein login is enabled by providing a login mask which is provided by medical network software (MedPort), which medical network software (MedPort) is configured to connect medical users being members of a medical user group with one another in order to enable transfer of medical data, in particular medical image data, between them.

L) The electronic network according to the preceding embodiment and/or according to one of the embodiments of the MeDPAP invention, wherein the medical data is part of a patient data set, access rights for members of the medical user group to the patient data set being controlled by an owner of the patient data set.

M) The electronic network according to any one of the three preceding embodiments and/or according to one of the embodiments of the MeDPAP invention, wherein the medical data is part of a patient data set and wherein after deleting the patient data set no client user can access the patient data set.

N) A method of configuring a virtual machine, in particular the VM of an embodiment of the MeDPAP invention, the virtual machine (VM) being a simulation of a computer and being configured for processing digital data, in particular medical data, by executing a digital data processing application program, in particular a medical data processing application program (MeDPAP), the method comprising:
  a) configuring the virtual machine (VM) to comprise a volatile memory (ViMStor) which is configured to comprise storage space for temporary data (TEMP) for temporarily storing the digital data;
  b) configuring the virtual machine (VM) to be accessed by any virtual machine user activated on a virtual machine user list, and denying any maintenance virtual machine user any permission regarding the storage space for temporary data (TEMP), wherein the denying is performed by logging into the virtual machine (VM) as an administrator and setting corresponding options;
  c) deactivating any administrator on the virtual machine user list by logging into the virtual machine (VM) as an administrator, setting corresponding options for each administrator in the virtual machine user list;
  d) logging off the administrator after deactivating the administrator on the virtual machine user list.

O) A program which, when running on a computer or when loaded onto a computer, causes the computer to perform one or more of the method steps of the method according to the preceding embodiment and/or a data storage medium on which the program is stored and/or a computer on which the program is running or into the memory of which the program is loaded and/or a signal wave carrying information which represents the program.

The invention claimed is:

1. A system comprising a processor coupled to a memory having stored thereon a virtual machine for processing digital data, in particular medical data by executing an executable digital data processing application program, in particular a medical data application program called MeDPAP, the virtual machine, when executed by the processor, is a simulation of a computer, the virtual machine being a simulation of a server, the virtual machine comprising at least the following components:
  a MeDPAP controller which is running on the virtual machine and which is constituted
    so that it can be addressed by a Uniform Resource Identifier called VM-URI via a wide area network,
    to support direct interoperable interaction with a client application over the wide area network,
    to assign a Uniform Resource Identifier called MeD-PAP-URI to the MeDPAP, and
    to send the assigned MeDPAP-URI to the client application via the wide area network; and
  the MeDPAP which is running on the virtual machine and which is constituted
    to process the digital data,
    so that it can be directly addressed by the client application via the wide area network by using the MeDPAP-URI, such that the MeDPAP can be addressed without needing the MeDPAP controller or a web service as an interface, and
    to support direct interaction with the client application over the wide area network for receiving instructions from the client application to process the digital data,
  wherein the virtual machine is constituted so that a plurality of the MeDPAPs can be executed on the virtual machine;
  herein the MeDPAP controller is constituted
    to respectively assign individual MeDPAP-URIs (URIi) to the MeDPAPs and to store the respective assignment between the MeDPAP-URIs and MeDPAPs,
    to be addressable by a plurality of the client applications via the wide area network (WAN) by using the VM-URI,
    to respectively and exclusively assign one of the MeDPAP-URIs (URIi) to one of the MeDPAPs, and
    to respectively send the assigned MeDPAP-URIs to the assigned client applications; and
  wherein the MeDPAP is constituted so that if the plurality of MeDPAPs are executed on the VM, the MeDPAPs can be respectively addressed by one of the plurality of the client applications via the wide area network (WAN) by using the sent and assigned individual MeDPAP-URI (URIi) and respectively support direct interaction with the client applications over the wide area network (WAN) for receiving instructions from the client applications to process the digital data, wherein there is a bijective direct communication between the individual client applications and the individual MeDPAPs so that one MeDPAP is processing the digital data only for one client application.

2. The system of claim 1, comprising:
  wherein the MeDPAP is constituted
    to store a file of the processed digital data called Prodaf in a storage space,
    to translate a location of the Prodaf into an individual Unique Resource Identifier called Prodaf-URI, and
    to send the Prodaf-URI to the client application via the wide area network;
  wherein the MeDPAP controller is constituted
    to re-translate the Prodaf-URI received from the client application via the wide area network into the location of the Prodaf,
    to read the Prodaf by using the re-translated storage location, and
    to send the Prodaf to the client application via the wide area network.

3. The system of claim 1, wherein
the MeDPAP is constituted
to store a file of the processed digital data called Prodaf in a storage space,
to translate a location of the Prodaf into an individual Unique Resource Identifier called Prodaf-URI, and
to send the Prodaf-URI to the client application via the wide area network;
wherein the MeDPAP controller is constituted
to re-translate the Prodaf-URI received from the client application via the wide area network into the location of the Prodaf,
to read the Prodaf by using the re-translated storage location, and
to send the Prodaf to the client application via the wide area network
the virtual machine comprises a VM data storage for storing the digital data to be processed and/or the processed digital data;
the MeDPAP controller is constituted to respectively and exclusively assign one of the storage spaces within the VM data storage to one of the MeDPAPs;
the MeDPAPs are respectively constituted to respectively store the Prodafs only in the respectively and exclusively assigned storage spaces; and
the MeDPAP controller is constituted to look for a respective one the Prodafs only within the one of the storage spaces respectively and exclusively assigned to that one of the MeDPAPs which has generated the respective one of the Prodafs.

4. The system of claim 3, wherein the MeDPAP controller is constituted
to generate an individual identifier called VM session ID for each communication session with one of the client applications;
to send the VM session ID to the respective client application;
to respectively assign the storage spaces to the VM session IDs; and
to receive the VM session ID in addition to the request to read the Prodaf from the client application, and
to look for the Prodaf only within the storage space assigned to the received VM session ID.

5. The system of claim 4, wherein the MeDPAP is configured
to receive a session ID called portal session ID from the client application;
to store the received portal session ID;
to check a later received portal session ID whether it corresponds to the stored portal session, and
to process the digital data only if the checking results indicates a correspondence.

6. The system according to claim 5, wherein the MeDPAP controller is constituted
to stop a MeDPAP and to erase the content in the storage space assigned to the stopped MeDPAP; and
to start a new MeDPAP and wherein
the MeDPAP controller and/or the new MeDPAP is constituted to check whether the storage space assigned to the new MeDPAP is empty and/or to erase the content in the assigned storage space when the new MeDPAP is started.

7. The system of claim 5, wherein the MeDPAP controller is constituted to
respectively and exclusively assign one of the executed MeDPAPs to one of the communication sessions;
to monitor the number of MeDPAPs assigned to the communication sessions;
to report the number to a server application called login server application;
to receive instruction from the login server application to start a new virtual machine;
and to start the new virtual machine in response to the instruction.

8. The system according to claim 1, wherein the MeDPAP controller is constituted to start a new MeDPAP in order to maintain the number of MeDPAPs irrespective of the number of client applications communicating with the MeDPAP controller.

9. The system of claim 1, wherein the MeDPAP controller is constituted
to respectively generate the VM session IDs for the communication sessions with the client applications;
to receive a session ID called portal session ID from each one of the client applications which portal session ID is individual for each client application and which origins from a server application
to send the portal session ID to the server application
to receive an acknowledgement from the server application according to which the portal session ID is valid or not; and
to send the VM session ID to the client application only if the portal session ID is valid.

10. A non-transient data storage medium comprising system image data describing a system image of a virtual machine, the virtual machine being for processing digital data, in particular medical data by executing an executable digital data processing application program, in particular a medical data application program called MeDPAP, the virtual machine being a simulation of a computer, the simulation running on a computer system, the virtual machine being a simulation of a server, the virtual machine comprising at least the following components:
a MeDPAP controller which is running on the virtual machine and which is constituted
so that it can be addressed by a Uniform Resource Identifier called VM-URI via a wide area network,
to support direct interoperable interaction with a client application over the wide area network,
to assign a Uniform Resource Identifier called MeDPAP-URI to the MeDPAP, and
to send the assigned MeDPAP-URI to the client application via the wide area network; and
the MeDPAP which is running on the virtual machine and which is constituted
to process the digital data,
so that it can be directly addressed by the client application via the wide area network by using the MeDPAP-URI, such that the MeDPAP can be addressed without needing the MeDPAP controller or a web service as an interface, and
to support direct interaction with the client application over the wide area network for receiving instructions from the client application to process the digital data,
wherein the virtual machine is constituted so that a plurality of the MeDPAPs can be executed on the virtual machine;
wherein the MeDPAP controller is constituted
to respectively assign individual MeDPAP-URIs (URIi) to the MeDPAPs and to store the respective assignment between the MeDPAP-URIs and MeDPAPs, to be addressable by a plurality of the client applications via the wide area network (WAN) by using the VM-URI,
to respectively and exclusively assign one of the MeDPAP-URIs (URIi) to one of the MeDPAPs, and
to respectively send the assigned MeDPAP-URIs to the assigned client applications; and
wherein the MeDPAP is constituted so that if the plurality of MeDPAPs are executed on the VM, the MeDPAPs can be respectively addressed by one of the plurality of the client applications via the wide area network (WAN) by using the sent and assigned individual MeDPAP-URI (URIi) and respectively support direct interaction with the client applications over the wide area network (WAN) for receiving instructions from the client applications to process the digital data, wherein there is a bijective direct communication between the individual client applications and the individual MeDPAPs so that one MeDPAP is processing the digital data only for one client application.

11. A cloud computer system comprising a number of computers, wherein a plurality of virtual machines are running on the cloud computer system, the virtual machines being for processing digital data, in particular medical data by executing an executable digital data processing application program, in particular a medical data application program called MeDPAP, the virtual machine being a simulation of a computer, the simulation running on a computer system, the virtual machine being a simulation of a server, the virtual machine comprising at least the following components:
   a MeDPAP controller which is running on the virtual machine and which is constituted
      so that it can be addressed by a Uniform Resource Identifier called VM-URI via a wide area network,
      to support direct interoperable interaction with a client application over the wide area network,
      to assign a Uniform Resource Identifier called MeDPAP-URI to the MeDPAP, and
      to send the assigned MeDPAP-URI to the client application via the wide area network; and
   the MeDPAP which is running on the virtual machine and which is constituted
      to process the digital data,
      so that it can be directly addressed by the client application via the wide area network by using the MeDPAP-URI, such that the MeDPAP can be addressed without needing the MeDPAP controller or a web service as an interface, and
      to support direct interaction with the client application over the wide area network for receiving instructions from the client application to process the digital data,
   wherein the virtual machine is constituted so that a plurality of the MeDPAPs can be executed on the virtual machine;
   wherein the MeDPAP controller is constituted
      to respectively assign individual MeDPAP-URIs (URIi) to the MeDPAPs and to store the respective assignment between the MeDPAP-URIs and MeDPAPs,
      to be addressable by a plurality of the client applications via the wide area network (WAN) by using the VM-URI,
      to respectively and exclusively assign one of the MeDPAP-URIs (URIi) to one of the MeDPAPs, and
      to respectively send the assigned MeDPAP-URIs to the assigned client applications; and
   wherein the MeDPAP is constituted so that if the plurality of MeDPAPs are executed on the VM, the MeDPAPs can be respectively addressed by one of the plurality of the client applications via the wide area network (WAN) by using the sent and assigned individual MeDPAP-URI (URIi) and respectively support direct interaction with the client applications over the wide area network (WAN) for receiving instructions from the client applications to process the digital data, wherein there is a bijective direct communication between the individual client applications and the individual MeDPAPs so that one MeDPAP is processing the digital data only for one client application.

12. An electronic network system comprising:
   the cloud computer system of claim 11;
   a plurality of client computers on which the plurality of client applications are running and which are connected to the cloud computer system via the wide area network to exchange data with the MeDPAP controller by using the VM-URI and to respectively exchange data with the MeDPAPs by using the MeDPAP-URIs respectively and exclusively assigned to one of the client applications so that only one client application is communicating with one MeDPAP.

13. A method of transforming a virtual machine, comprising the steps of
   a) logging in to the virtual machine to be transformed; and
   b) i) loading a system image of another virtual machine into the virtual machine to be transformed or ii) installing the components of the other virtual machine on the virtual machine to be transformed, wherein the other virtual machine is a virtual machine for processing digital data, in particular medical data by executing an executable digital data processing application program, in particular a medical data application program called MeDPAP, the virtual machine being a simulation of a computer, the simulation running on a computer system, the virtual machine being a simulation of a server, the virtual machine comprising at least the following components:
      a MeDPAP controller which is running on the virtual machine and which is constituted
         so that it can be addressed by a Uniform Resource Identifier called VM-URI via a wide area network,
         to support direct interoperable interaction with a client application over the wide area network,
         to assign a Uniform Resource Identifier called MeDPAP-URI to the MeDPAP, and
         to send the assigned MeDPAP-URI to the client application via the wide area network; and
      the MeDPAP which is running on the virtual machine and which is constituted
         to process the digital data,
         so that it can be directly addressed by the client application via the wide area network by using the MeDPAP-URI, such that the MeDPAP can be addressed without needing the MeDPAP controller or a web service as an interface, and
         to support direct interaction with the client application over the wide area network for receiving instructions from the client application to process the digital data,
      wherein the virtual machine is constituted so that a plurality of the MeDPAPs can be executed on the virtual machine;

wherein the MeDPAP controller is constituted
  to respectively assign individual MeDPAP-URIs (URIi) to the MeDPAPs and to store the respective assignment between the MeDPAP-URIs and MeDPAPs,
  to be addressable by a plurality of the client applications via the wide area network (WAN) by using the VM-URI,
  to respectively and exclusively assign one of the MeDPAP-URIs (URIi) to one of the MeDPAPs, and
  to respectively send the assigned MeDPAP-URIs to the assigned client applications; and
wherein the MeDPAP is constituted so that if the plurality of MeDPAPs are executed on the VM, the MeDPAPs can be respectively addressed by one of the plurality of the client applications via the wide area network (WAN) by using the sent and assigned individual MeDPAP-URI (URIi) and respectively support direct interaction with the client applications over the wide area network (WAN) for receiving instructions from the client applications to process the digital data, wherein there is a bijective direct communication between the individual client applications and the individual MeDPAPs so that one MeDPAP is processing the digital data only for one client application.

14. A non-transient program storage medium on which a program is stored, which, when running on a computer or when loaded onto a computer, causes the computer to performs steps as follows:
   a) logging in to a virtual machine to be transformed; and
   b) i) loading a system image of another virtual machine into the virtual machine to be transformed or ii) installing the components of the other virtual machine on the virtual machine to be transformed, wherein the other virtual machine is a virtual machine for processing digital data, in particular medical data by executing an executable digital data processing application program, in particular a medical data application program called MeDPAP, the virtual machine being a simulation of a computer, the simulation running on a computer system, the virtual machine being a simulation of a server, the virtual machine comprising at least the following components:
   a MeDPAP controller which is running on the virtual machine and which is constituted
     so that it can be addressed by a Uniform Resource Identifier called VM-URI via a wide area network,
     to support direct interoperable interaction with a client application over the wide area network,
     to assign a Uniform Resource Identifier called MeDPAP-URI to the MeDPAP, and
     to send the assigned MeDPAP-URI to the client application via the wide area network; and
   the MeDPAP which is running on the virtual machine and which is constituted
     to process the digital data,
     so that it can be directly addressed by the client application via the wide area network by using the MeDPAP-URI, such that the MeDPAP can be addressed without needing the MeDPAP controller or a web service as an interface, and
     to support direct interaction with the client application over the wide area network for receiving instructions from the client application to process the digital data,
   wherein the virtual machine is constituted so that a plurality of the MeDPAPs can be executed on the virtual machine;
   wherein the MeDPAP controller is constituted
     to respectively assign individual MeDPAP-URIs (URIi) to the MeDPAPs and to store the respective assignment between the MeDPAP-URIs and MeDPAPs,
     to be addressable by a plurality of the client applications via the wide area network (WAN) by using the VM-URI,
     to respectively and exclusively assign one of the MeDPAP-URIs (URIi) to one of the MeDPAPs, and
     to respectively send the assigned MeDPAP-URIs to the assigned client applications; and
   wherein the MeDPAP is constituted so that if the plurality of MeDPAPs are executed on the VM, the MeDPAPs can be respectively addressed by one of the plurality of the client applications via the wide area network (WAN) by using the sent and assigned individual MeDPAP-URI (URIi) and respectively support direct interaction with the client applications over the wide area network (WAN) for receiving instructions from the client applications to process the digital data, wherein there is a bijective direct communication between the individual client applications and the individual MeDPAPs so that one MeDPAP is processing the digital data only for one client application.

15. A computer comprising the non-transient program storage medium of claim 14.

* * * * *